(12) United States Patent
Genova et al.

(10) Patent No.: US 11,154,180 B2
(45) Date of Patent: Oct. 26, 2021

(54) CAMERA POSITIONING SYSTEM, METHOD, AND APPARATUS FOR CAPTURING IMAGES DURING A MEDICAL PROCEDURE

(71) Applicant: Titan Medical Inc., Toronto (CA)

(72) Inventors: Perry A. Genova, Chapel Hill, NC (US); Hans Christian Pflaumer, Apex, NC (US); Aki Hannu Einari Laakso, Raleigh, NC (US); Allan Katz, Farmingdale, NY (US); Alejandro Espinosa, Miramar, FL (US); Eduardo A. Ampuero, Miramar, FL (US); Duane Couri, Miramar, FL (US)

(73) Assignee: TITAN MEDICAL INC., Toronto (CA)

( * ) Notice: Subject to any disclaimer, the term of this patent is extended or adjusted under 35 U.S.C. 154(b) by 137 days.

(21) Appl. No.: 16/435,170

(22) Filed: Jun. 7, 2019

(65) Prior Publication Data

US 2020/0113417 A1    Apr. 16, 2020

Related U.S. Application Data

(63) Continuation of application No. 16/156,625, filed on Oct. 10, 2018, now Pat. No. 10,398,287.

(51) Int. Cl.
*A61B 1/00* (2006.01)
*A61B 1/05* (2006.01)
(Continued)

(52) U.S. Cl.
CPC ........ *A61B 1/00066* (2013.01); *A61B 1/0016* (2013.01); *A61B 1/0051* (2013.01);
(Continued)

(58) Field of Classification Search
CPC . A61B 1/00133; A61B 1/0016; A61B 1/0052; A61B 1/0055; A61B 1/008; A61B 1/05; A61B 1/051
See application file for complete search history.

(56) References Cited

U.S. PATENT DOCUMENTS

| | | | |
|---|---|---|---|
| 4,991,957 A * | 2/1991 | Sakamoto | A61B 1/0005 356/241.4 |
| 5,235,965 A | 8/1993 | Hiroya | |
| (Continued) | | | |

OTHER PUBLICATIONS

Advanced Sterilization Products, "Sterrad 100NX," downloaded on Oct. 8, 2018 from https://www.emea.aspjj.com/sites/aspjj.com.emea/files/pdf/STERRADFF_FamilyOfProducts_0.pdf, in 12 pages.
(Continued)

*Primary Examiner* — Aaron B Fairchild

(57) ABSTRACT

In some embodiments, a visualization device for a robotic surgery apparatus can include a housing configured to be removably attached to a mounting interface of the apparatus and be positioned adjacent an insertion device of the apparatus. The housing can include first and second openings positioned on an exterior of the housing. The housing can include a substantially flexible camera tube with a first end attached to the housing and a second end including at least one camera. The second end can be inserted through the first opening in the housing, pass through interior of the housing, and exit the housing through the second opening in the housing. The second end can extend away from the housing toward a region of interest outside the housing or retract away from the region of interest and back toward the housing. The camera tube can form a loop around a portion of the housing.

27 Claims, 30 Drawing Sheets

(51) Int. Cl.
*A61B 1/005* (2006.01)
*A61B 1/06* (2006.01)
*A61B 34/30* (2016.01)
A61B 90/00 (2016.01)
A61B 90/30 (2016.01)
A61B 34/00 (2016.01)
*A61B 1/07* (2006.01)

(52) U.S. Cl.
CPC ........ *A61B 1/0052* (2013.01); *A61B 1/00071* (2013.01); *A61B 1/00105* (2013.01); *A61B 1/00112* (2013.01); *A61B 1/00121* (2013.01); *A61B 1/00128* (2013.01); *A61B 1/00133* (2013.01); *A61B 1/00135* (2013.01); *A61B 1/00142* (2013.01); *A61B 1/00154* (2013.01); *A61B 1/00193* (2013.01); *A61B 1/05* (2013.01); *A61B 1/06* (2013.01); *A61B 34/30* (2016.02); *A61B 1/0057* (2013.01); *A61B 1/00149* (2013.01); *A61B 1/00177* (2013.01); *A61B 1/00179* (2013.01); *A61B 1/00181* (2013.01); *A61B 1/053* (2013.01); *A61B 1/0684* (2013.01); *A61B 1/07* (2013.01); *A61B 34/71* (2016.02); *A61B 2090/306* (2016.02); *A61B 2090/309* (2016.02); *A61B 2090/371* (2016.02)

(56) References Cited

U.S. PATENT DOCUMENTS

| | | | |
|---|---|---|---|
| 5,299,559 A | | 4/1994 | Bruce et al. |
| 6,352,503 B1* | | 3/2002 | Matsui ............... A61B 17/1285 600/104 |
| 9,271,637 B2 | | 3/2016 | Farr |
| 9,358,072 B2* | | 6/2016 | Ullrich ................... A61B 34/77 |
| 9,801,551 B2 | | 10/2017 | Herzlinger et al. |
| 9,877,744 B2 | | 1/2018 | Cooper et al. |
| 10,011,018 B2 | | 7/2018 | McGrogan et al. |
| 2003/0176770 A1* | | 9/2003 | Merril ................... A61B 34/76 600/118 |
| 2003/0233024 A1 | | 12/2003 | Ando |
| 2005/0272975 A1* | | 12/2005 | McWeeney ....... A61M 25/0068 600/113 |
| 2006/0252993 A1 | | 11/2006 | Freed et al. |
| 2007/0043338 A1 | | 2/2007 | Moll et al. |
| 2007/0135803 A1 | | 6/2007 | Belson |
| 2007/0238927 A1 | | 10/2007 | Ueno et al. |
| 2008/0033450 A1 | | 2/2008 | Bayer et al. |
| 2011/0208000 A1 | | 8/2011 | Honda et al. |
| 2013/0282041 A1 | | 10/2013 | Gunday et al. |
| 2014/0107417 A1 | | 4/2014 | McKinley et al. |
| 2015/0057537 A1* | | 2/2015 | Dillon .................. A61B 1/0125 600/431 |

OTHER PUBLICATIONS

Intuitive Surgical, "da Vinci SP," downloaded on Oct. 9, 2018 from https://www.intuitivesurgical.com/sp/, in 5 pages.
Olympus America, "Rigid Laparoscopes," downloaded on Oct. 8, 2018 from http://medical.olympusamerica.com/products/rigid-laparoscopes, in 2 pages.
Non-Final Office Action dated Dec. 26, 2018 in U.S. Appl. No. 16/156,625, in 29 pages.
International Search Report dated Jan. 23, 2020 in International Application No. PCT/US2019/055255, in 5 pages.

* cited by examiner

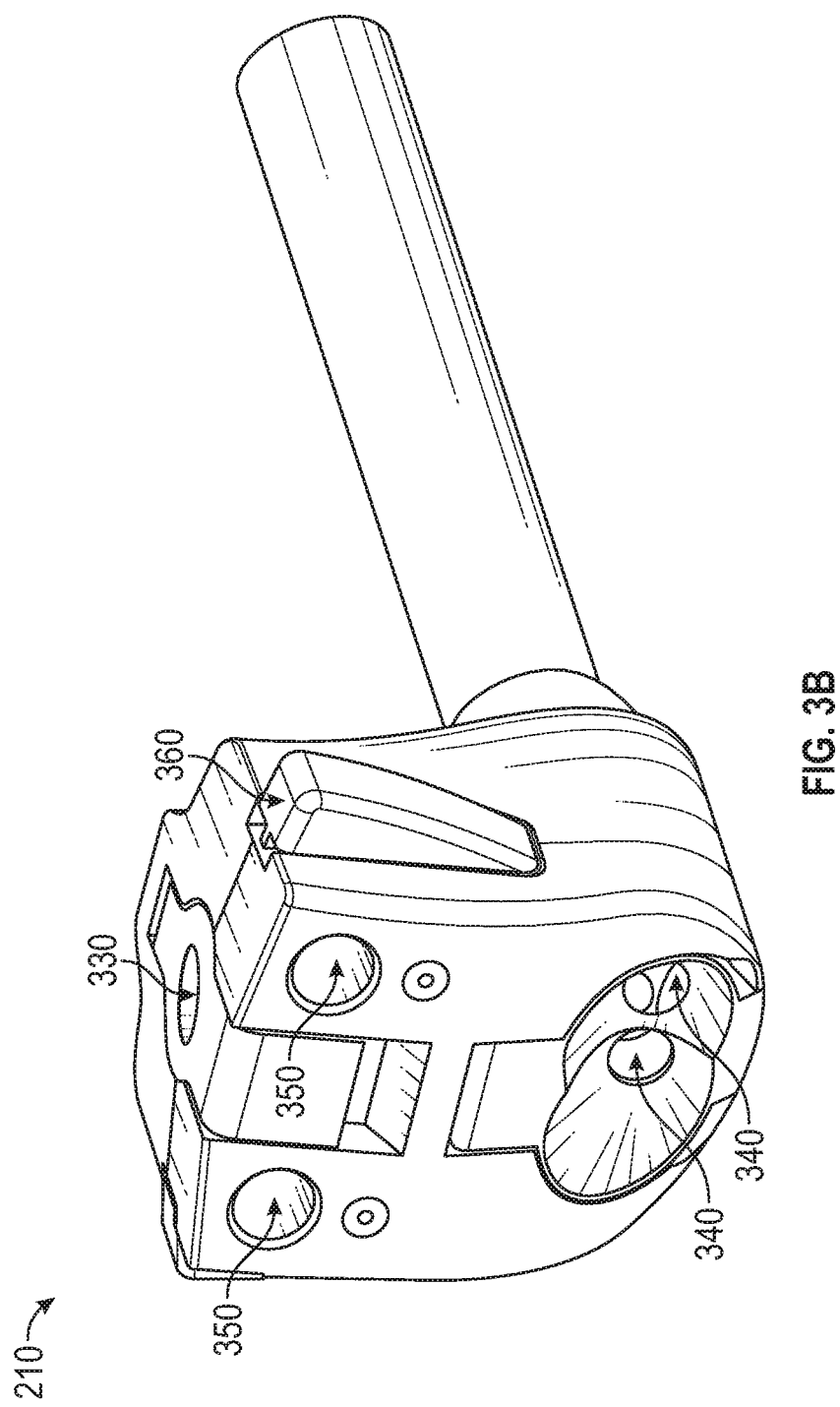

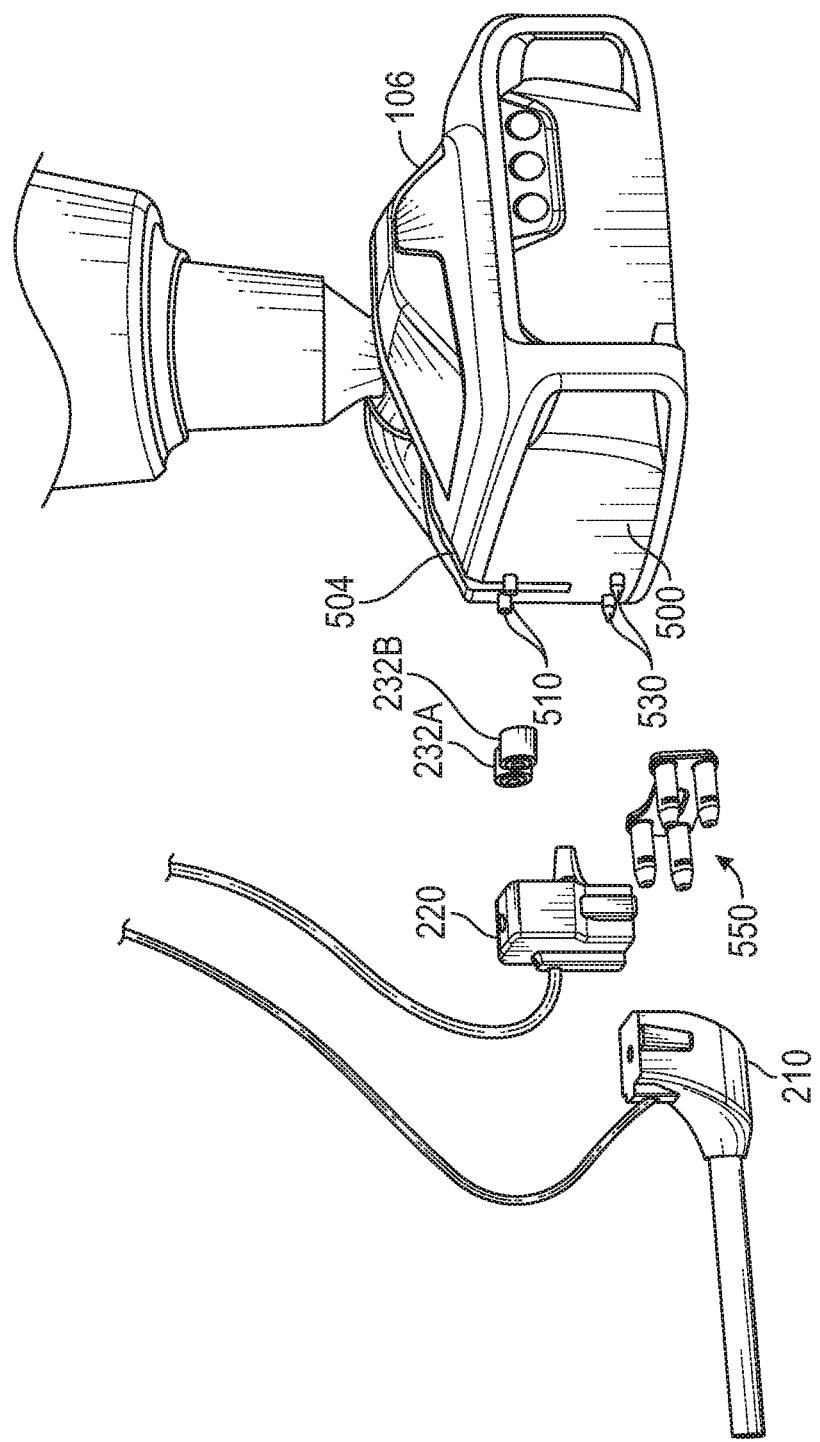

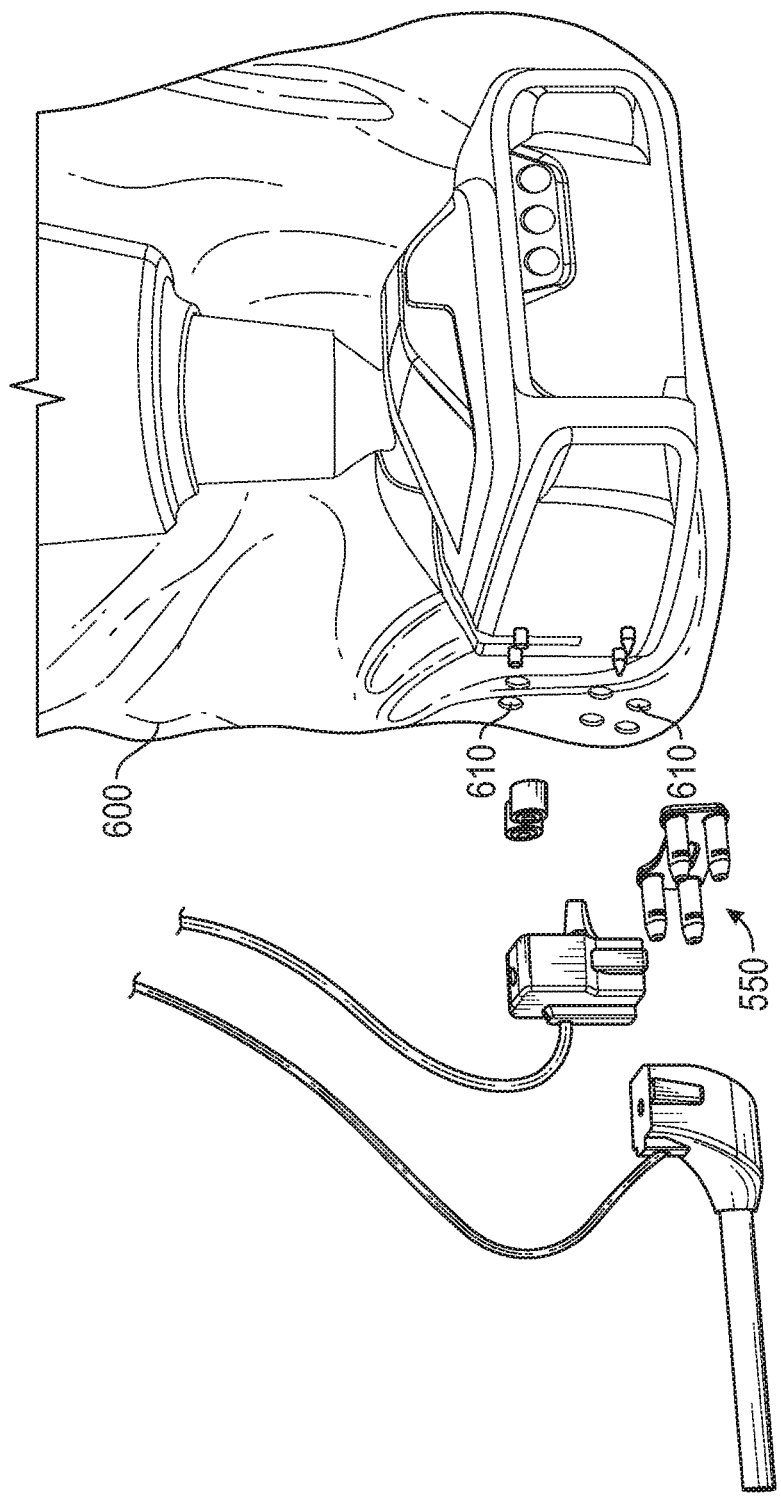

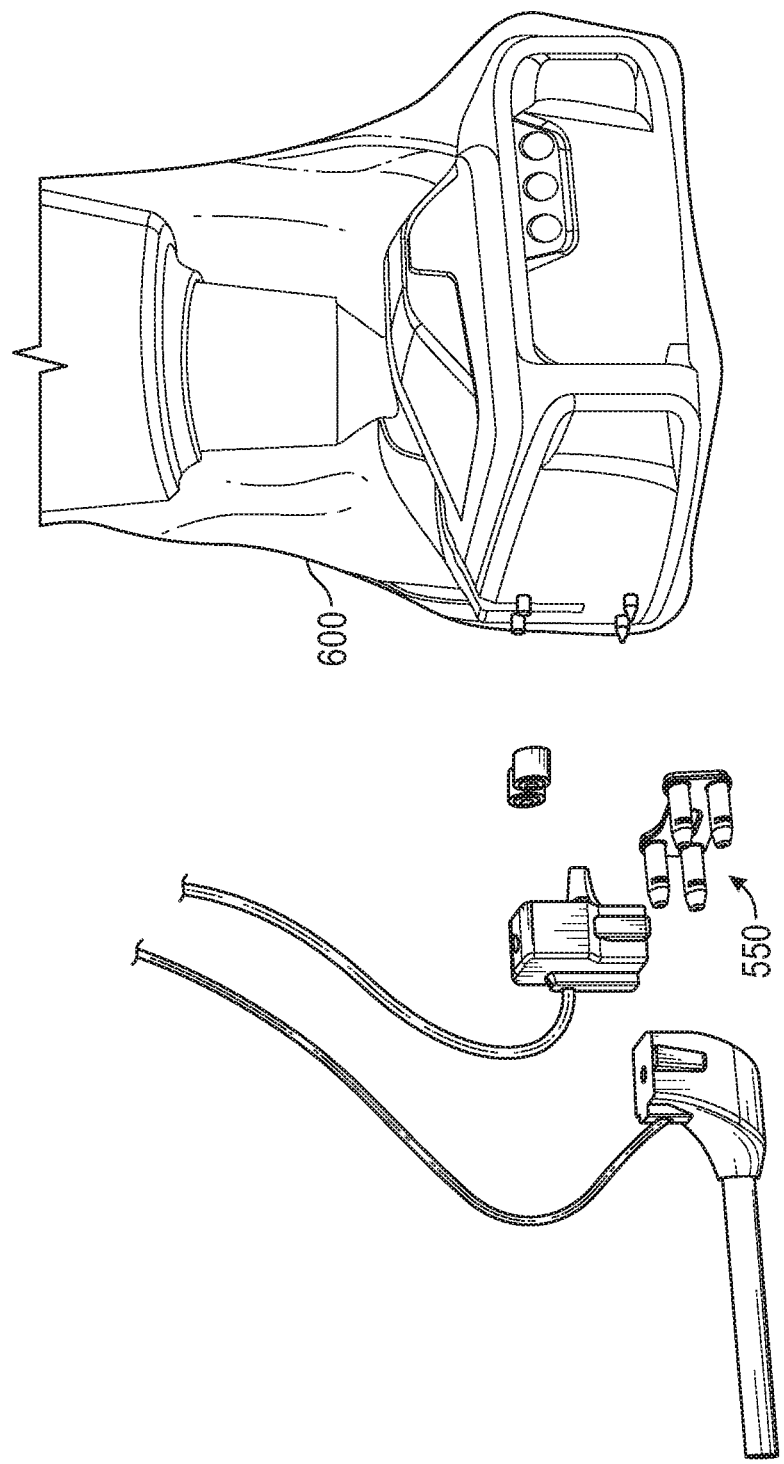

CAMERA POSITIONING SYSTEM, METHOD, AND APPARATUS FOR CAPTURING IMAGES DURING A MEDICAL PROCEDURE

CROSS-REFERENCE TO RELATED APPLICATIONS

This application is a continuation of U.S. patent application Ser. No. 16/156,625, filed on Oct. 10, 2018, entitled "CAMERA POSITIONING SYSTEM, METHOD, AND APPARATUS FOR CAPTURING IMAGES DURING A MEDICAL PROCEDURE," the disclosure of which is hereby incorporated by reference in its entirety.

TECHNICAL FIELD

This disclosure relates generally to positioning a camera for imaging and more particularly to positioning a camera inside a body cavity of a patient for capturing images during a medical procedure.

DESCRIPTION OF RELATED ART

Miniaturized cameras are used during investigative medical procedures and surgical procedures, such as laparoscopic surgery and computer assisted robotic surgery, to produce images of a site of the procedure within a body cavity of the patient. A camera generally includes an illumination source for illuminating the site of the procedure and a lens for capturing images of the site. Known camera systems suffer from a variety of shortcomings, including large size, poor resolution, obstacles with being sterilized, lack of reliability, difficulties with being replaced during medical procedure, and the like. The present disclosure overcomes these and other problems associated with known camera systems, methods, and apparatuses.

SUMMARY

In some cases, a visualization device for a single port robotic surgery apparatus can include a housing configured to be positioned adjacent an insertion device of the robotic surgery apparatus and be attached to a mounting interface of the robotic surgery apparatus, the housing including an interior portion and a plurality of openings, at least some of the plurality of openings positioned on an exterior surface of the housing. The visualization device can also include a camera tube including a first end attached to the housing and a second end including at least one camera, the second end configured to be inserted through a first opening of the plurality of openings in the housing, pass through the interior portion of the housing, extend outside the housing through a second opening of the plurality of openings in the housing, and enter a channel in the insertion device, the insertion of the second end causing the camera tube to form a loop. The visualization device can also include a drive opening in the housing configured to receive a plurality of rollers configured to abut a portion of the camera tube that passes through the drive opening when the second end is inserted through the first opening, the plurality of rollers configured to move the portion of the camera tube through the drive opening and cause the second end of the camera tube to extend away from the housing through the second opening or retract back toward or inside the housing when the second end is inserted through the first opening.

The visualization device of any of preceding paragraphs and/or any of visualization devices described below can include one or more of the following features. The plurality of rollers can be configured to be rotated in first and second directions by a plurality of pins positioned on the exterior of the mounting interface of the robotic surgery apparatus, the plurality of pins can be configured to be actuated by at least one motor of the robotic surgery apparatus, the second direction opposite the first direction. Rotation of the plurality of rollers in the first direction can cause the second end of the camera tube to extend away from the housing through the second opening. Rotation of the plurality of rollers in the second direction can cause the second end of the camera tube to retract back toward or inside the housing.

The visualization device of any of preceding paragraphs and/or any of visualization devices described below can include one or more of the following features. The device can include a plurality of openings positioned on the exterior of the housing and configured to removably receive a plurality of supporting pins attached to the mounting interface of the robotic surgery apparatus. Rotation of the plurality of rollers can cause a diameter of the loop formed by the camera tube to change. Rotation of the plurality of rollers in the first direction can cause the diameter of the loop to decrease and rotation of the plurality of rollers in the second direction can cause the diameter of the loop to increase.

The visualization device of any of preceding paragraphs and/or any of visualization devices described below can include one or more of the following features. The camera tube can be substantially flexible, the second end can include an articulating portion terminating in a face including the at least one camera, the articulating portion can be configured to cause at least one of a pan or tilt of the face including the at least one camera, and the articulating portion can be substantially rigid to generally maintain orientation of the face including the at least one camera in a plane parallel to a plane of the channel of the insertion device when the articulating portion of the second end is passed through and exits the channel.

The visualization device of any of preceding paragraphs and/or any of visualization devices described below can include one or more of the following features. The visualization device can include at least one actuator positioned on the exterior of the housing and configured to be actuated by at least one motor of the robotic surgery apparatus when the housing is attached to the mounting interface of the robotic surgery apparatus, the at least one actuator configured to change a shape of the articulating portion to cause at least one of the pan or tilt of the face including the at least one camera. A change of the shape can include forming at least one bend in the articulating portion. The camera tube can enclose a plurality of links configured to be pushed or pulled to change the shape of the articulating portion to cause at least one of the pan or tilt of the face including the at least one camera, and actuation of the at least one actuator can cause at least one cable of the plurality of cables to be pushed or pulled.

The visualization device of any of preceding paragraphs and/or any of visualization devices described below can include one or more of the following features. At least one camera can include two cameras configured to provide a stereoscopic image of a region of interest in the body cavity, and the device further can include a light source configured to illuminate the region of interest. Plurality of rollers can include surfaces with a friction coefficient that allows the plurality of rollers to slip along the portion of the camera tube that passes through the drive opening of the housing to prevent movement of the portion of the camera tube. Plurality of rollers can provide a sterile barrier between a sterile camera tube and non-sterile mounting interface of the robotic surgery apparatus when the housing is attached to the mounting interface of the robotic surgery apparatus.

In some cases, a kit including the visualization device of any of preceding paragraphs and/or any of visualization devices described below and the plurality of rollers can be provided. The housing, camera tube, and the plurality of rollers can be sterile.

In some cases, visualization device for a single port robotic surgery apparatus can include a housing configured to be removably attached to a mounting interface of the robotic surgery apparatus and be positioned adjacent an insertion device of the robotic surgery apparatus, the housing including first and second openings positioned on an exterior of the housing. The visualization device can also include a substantially flexible camera tube including a first end attached to the housing and a second end including at least one camera, the second end configured to be inserted through the first opening in the housing, pass through an interior of the housing, and exit the housing through the second opening in the housing, the second end configured to extend away from the housing toward a region of interest outside the housing or retract away from the region of interest and back toward the housing.

The visualization device of any of preceding paragraphs and/or any of visualization devices described below can include one or more of the following features. The housing can be configured to receive at least one driver configured to cause movement of the camera tube away from the housing and/or toward the housing. The region of interest can include a body cavity into which an end effector is configured to be inserted. The first end of the camera tube can be removably attached to the housing. The camera tube can be configured to form a loop around at least a portion of the housing.

The visualization device of any of preceding paragraphs and/or any of visualization devices described below can include one or more of the following features. At least one driver can include a plurality of rollers configured to contact the camera tube and advance the camera tube toward the region of interest and retract the camera tube away from the region of interest. Rotation of the plurality of rollers in the first direction can cause the camera tube to advance and a diameter of the loop to decrease. Rotation of the plurality of rollers in the second direction opposite to the first direction can causes the camera tube to retract and diameter of the loop to increase.

In some cases, a robotic surgery apparatus including a mounting interface configured to support visualization device of any of preceding paragraphs or any of visualization devices described below can be provided.

In some cases, a kit including the visualization device of any of preceding paragraphs and/or any of visualization devices described below and the insertion device of any of preceding paragraphs and/or any of visualization devices described below can be provided. The insertion device can include a passage positioned in an interior volume of the insertion device. The passage can be configured to permit the second end of the camera tube to pass through and exit the insertion device. The insertion device can include at least one instrument channel configured to receive a surgical instrument. Central axis of at least a portion of the passage can be nonparallel with a central axis of the at least one instrument channel. At least one instrument channel can be substantially straight and at least a portion of the passage can be curved. The housing, camera tube, and the insertion device can be sterile.

Any of the visualization devices of any of preceding paragraphs and/or described below can be used with any of insertion devices and/or robotic surgery systems described herein.

In some cases, an insertion device for a single port robotic surgery apparatus can include a first portion including a plurality of instrument channels positioned in an interior of the first portion and extending along substantially an entire length of the first portion, the plurality of instrument channels configured to removably house a plurality of surgical instruments and first and second camera channels positioned in the interior of the first portion and extending along substantially the entire length of the first portion, the first camera channel configured to removably house a primary camera tube and the second camera channel comprising a secondary camera. The insertion device can also include a second portion including an insertion channel terminating at a first end with a first opening configured to permit the primary camera tube to pass through and terminating at a second end opposite the first end with a second opening aligned with the first camera channel of the first portion, the insertion channel configured to permit the primary camera tube to pass through the insertion channel and enter the first camera channel. The secondary camera facilitates insertion into a body cavity of at least one of the plurality of instruments or the primary camera tube.

The insertion device of any of preceding paragraphs and/or any of insertion devices described below can include one or more of the following features. The second portion can include at least one interface configured to engage and disengage at least one closure in order to attach and detach the second portion from the mounting interface of a robotic surgery apparatus. The second portion can include at least one opening configured to receive a pin positioned on the mounting interface of the robotic surgery apparatus, and wherein the at least one closure can be configured to engage and disengage the at least one pin. At least one closure can include a cam lock.

The insertion device of any of preceding paragraphs and/or any of insertion devices described below can include one or more of the following features. The first opening can be configured to be aligned with an opening in a visualization device including the primary camera tube, the alignment permitting the primary camera tube to pass through the insertion channel and the first camera channel. The first opening can be positioned on an exterior surface of the second portion configured to face a housing of the visualization device. The exterior surface of the second portion can include top exterior surface.

The insertion device of any of preceding paragraphs and/or any of insertion devices described below can include one or more of the following features. The first and second camera channels can be positioned on opposite sides of the first portion. A diameter of the first camera channel can be larger than a diameter of the second camera channel. The secondary camera can include a face positioned at a distal end of the first portion. The secondary camera can include a two-dimensional imager. The secondary camera can include an illumination device. The secondary camera can include an optical prism configured to redirect a detected image of at least a portion of the body cavity on an image sensor positioned in a different plane than the at least the portion of the body cavity. The first and second portions of the housing and the secondary camera can be sterile.

The insertion device of any of preceding paragraphs and/or any of insertion devices described below can include one or more of the following features. The insertion channel can include a curved portion, and wherein the plurality of instrument channels are substantially straight. Central axis of the curved portion of the insertion channel may be nonparallel with a central axis of at least one instrument channel.

In some cases, a kit including the insertion device of any of preceding paragraphs and/or any of insertion devices described below and the visualization device with the primary camera tube of any of preceding paragraphs and/or described below can be provided.

In some cases, an insertion device for a robotic surgery apparatus can include a first portion including first and second camera channels positioned in an interior of the first portion and extending along at least a portion of the first housing, the first camera channel configured to removably enclose a primary camera tube and the second camera channel configured to enclose a secondary camera. The insertion device can include a second portion including a passage configured to permit the primary camera tube to pass through, the passage aligned with the first camera channel to permit at least a portion the primary camera tube to enter the first camera channel, pass through the first camera channel, and exit the first camera channel.

The insertion device of any of preceding paragraphs and/or any of insertion devices described below can include one or more of the following features. The secondary camera can be integral with the second camera channel. The first portion can include an instrument channel extending along at least the portion of the housing, the instrument channel configured to removably enclose a surgical instrument.

The insertion device of any of preceding paragraphs and/or any of insertion devices described below can include one or more of the following features. The instrument channel can extend between a first instrument opening at a proximal end of the first portion and a second instrument opening at a distal end of the first portion, the distal end opposite the proximal end. At least one of the passage or the first instrument opening can include a substantially fluid impermeable seal. The passage can be positioned in an interior volume of the housing. Central axis of at least a portion of the passage can be nonparallel with a central axis of the instrument channel. At least a portion of the passage can be curved, and the instrument channel can be substantially straight. The passage can be configured to be aligned with an opening in a visualization device can include the primary camera tube, the alignment permitting the primary camera tube to pass through the passage and enter the first camera channel.

In some cases, a kit including the insertion device of any of preceding paragraphs and/or any of insertion devices described below and the visualization device of any of preceding paragraphs and/or described below can be provided. The insertion device and visualization device can be sterile.

In some cases, a method of operating a robotic surgery apparatus can include attaching an insertion device to a mounting interface of a robotic surgery apparatus. The method can include attaching a visualization device that includes a primary camera to the mounting interface. The method can be at least partially performed by a user, such as a nurse, surgeon, or the like. The insertion device and/or visualization device can include any of the features described in any of preceding paragraphs or below.

The method of any of preceding paragraphs and/or any of the methods described below can include one or more of the following features. A distal end of the primary camera can be inserted through one or more openings in the visualization device (as described in any of preceding paragraphs or below). The distal end of the primary camera can be advanced through the visualization device and into the insertion device (as described in any of preceding paragraphs or below). This can be performed by actuating one or more first actuators. The distal end of the primary camera can be advanced through the insertion device and exit the insertion device (as described in any of preceding paragraphs or below). The distal end can be advanced adjacent to or into a site of interest to obtain one or more images of at least a portion of the site of interest. At least one surgical instrument can be advanced adjacent to or into a site of interest through a channel in the insertion device. In use, the distal end of the primary camera can be advanced or retracted.

The method of any of preceding paragraphs and/or any of the methods described below can include one or more of the following features. The distal end of the primary camera can be articulated, such as panned and/or tilted, by actuating one or more second actuators. Actuating the one or more second actuators can cause one or more flexible links of the primary camera to be manipulated, which can cause articulation of the distal end. The one or more flexible links can be pushed and/or pulled. The insertion device can include a secondary camera that can provide one or more images of at least a portion of the site of interest.

The method of any of preceding paragraphs and/or any of the methods described below can include one or more of the following features. At least one of the insertion device, visualization device, or the primary camera can be sterile. The mounting interface of the robotic surgery apparatus can be non-sterile. A sterile drape can be placed over the mounting interface to provide a sterile barrier. One or more holes can be made in the drape to permit mounting the insertion device and visualization device through the drape. One or more drivers, such as rollers, configured to advance and/or retract the primary camera can be inserted into an opening in the visualization device. The one or more drivers can be attached to and actuated by the one or more first actuators, which can be positioned on the mounting interface of the robotic surgery apparatus. The one or more drivers can provide a sterile barrier between the one or more first actuators, which can be non-sterile, and the visualization device and primary camera, which can be sterile. One or more sterile covers can be used to provide a sterile barrier between other components of the mounting interface (for example, one or more pins, one or more second actuators, or the like) and one or more of the insertion device or visualization device.

Any of the insertion devices of any of preceding paragraphs and/or described below can be used with any of visualization devices and/or robotic surgery systems described herein.

In some cases, a kit including the insertion device of any of preceding paragraphs and/or any of insertion devices described below and the visualization device of any of preceding paragraphs and/or described below can be provided.

In some cases, a robotic surgery apparatus as described and/or illustrated is provided. In some cases, a visualization device as described and/or illustrated is provided. In some cases, an insertion device as described and/or illustrated is provided.

In some cases, a method of using and/or operating a robotic surgery apparatus as described and/or illustrated is provided. In some cases, a method of using and/or operating a visualization device as described and/or illustrated is provided. In some cases, a method of using and/or operating an insertion device as described and/or illustrated is provided.

BRIEF DESCRIPTION OF THE DRAWINGS

Embodiments of the present disclosure will now be described hereinafter, by way of example only, with reference to the accompanying drawings in which:

FIGS. 3A-3D illustrate an insertion device according to some embodiments;

FIGS. 6A-6I illustrate attachment of insertion and visualization devices to a mounting interface of a drive unit of a robotic surgery system according to some embodiments;

DETAILED DESCRIPTION

Overview

When performing medical procedures (for example, with assistance of surgery using a robotic surgical system) one or more instruments can be inserted into a body cavity of a patient. The insertion process has some risk since instruments may inadvertently damage organs or tissue while being inserted. Incorrect positioning of the one or more instruments in the body cavity may also result in a limited range of motion within the body cavity.

As an example, when performing abdominal surgery, at least one incision would be made in a body wall of the patient's abdomen. A trocar or other access port, may then be inserted through the incision. A camera can be first inserted through the access port and used by a surgeon to capture and relay stereoscopic images of a surgical site. One or more instruments can be inserted following the camera insertion. Views provided by the camera facilitate insertion of the one or more instruments and their manipulation of the surgical site.

Figure 1:
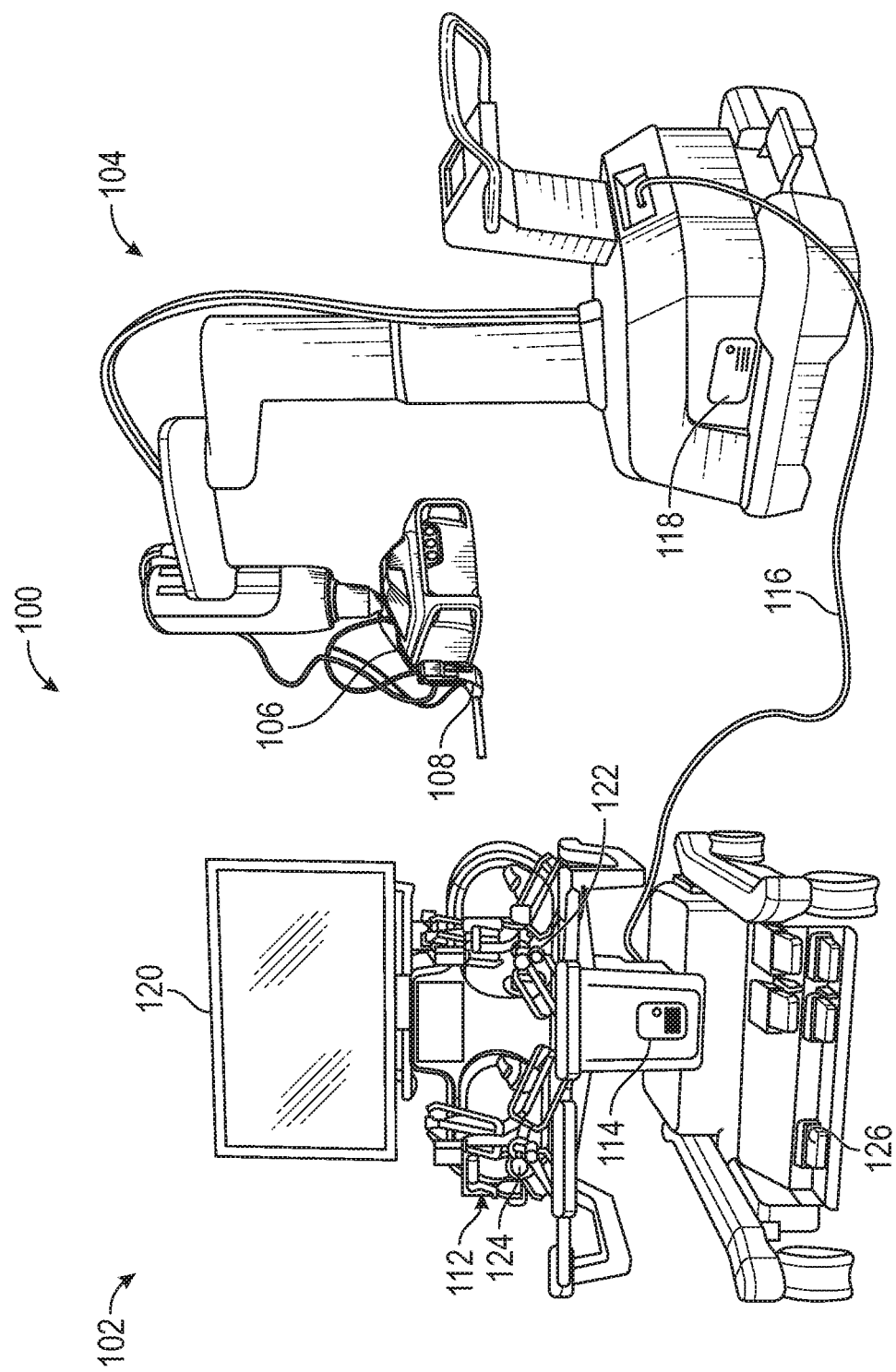
FIG. 1 illustrates a robotic surgery system in accordance with some embodiments.

Referring to FIG. 1, a robotic surgery system in accordance with some embodiments is shown generally at 100. In some implementations, the robotic surgery system 100 can be configured to facilitate a medical procedure performed via a single incision. A single access port can be inserted into the incision to provide access for one or more instruments and cameras.

The system 100 can include a workstation 102 and a patient cart 104. The patient cart 104 can include a central unit or drive unit 106 to which instrument insertion and visualization devices 108 can be attached or mounted. The workstation 102 can include an input device 112 that receives operator input and produces input signals and may also be configured to generate feedback to the operator. The feedback can be visual, auditory, haptic, or the like. The input device 112 can be implemented using a haptic interface available from Force Dimension, of Switzerland, for example.

The workstation 102 can further include a master processor circuit 114 in communication with the input device 112 for receiving the input signals and generating control signals for controlling the robotic surgery system, which can be transmitted to the patient cart 104 via an interface cable 116. In some cases, transmission can be wireless and interface cable 116 may not be present. The input device 112 can include right and left hand controllers 122 and 124, which are configured to be grasped by the operator's hands and moved to produce input signals at the input device 112. The patient cart 104 can include a slave processor circuit 118 that receives and the control signals from the master processor circuit 114 and produces slave control signals operable to control the instrument insertion and visualization devices 108 and one or more instruments (and their respective end effectors) during a surgical procedure. The one or more instruments can include dexterous tools, such as grippers, needle drivers, staplers, dissectors, cutters, hooks, graspers, scissors, coagulators, irrigators, suction devices, that are used for performing a surgical procedure. While both master and slave processor circuits are illustrated, in other embodiments a single processor circuit may be used to perform both master and slave functions. The workstation 102 can also include a user interface, such as a display 120 in communication with the master processor circuit 114 for displaying information (such as, body cavity images) for a region or site of interest (for example, a surgical site, a body cavity, or the like) and other information to an operator. The workstation 102 can also include one or more controllers, such as one or more pedals 126, for controlling the robotic surgery system. For example, one or more pedals 126 can include a clutch pedal that allows repositioning one or more controllers 122 or 124 without corresponding movement of the associated instrument.

Figure 2A:
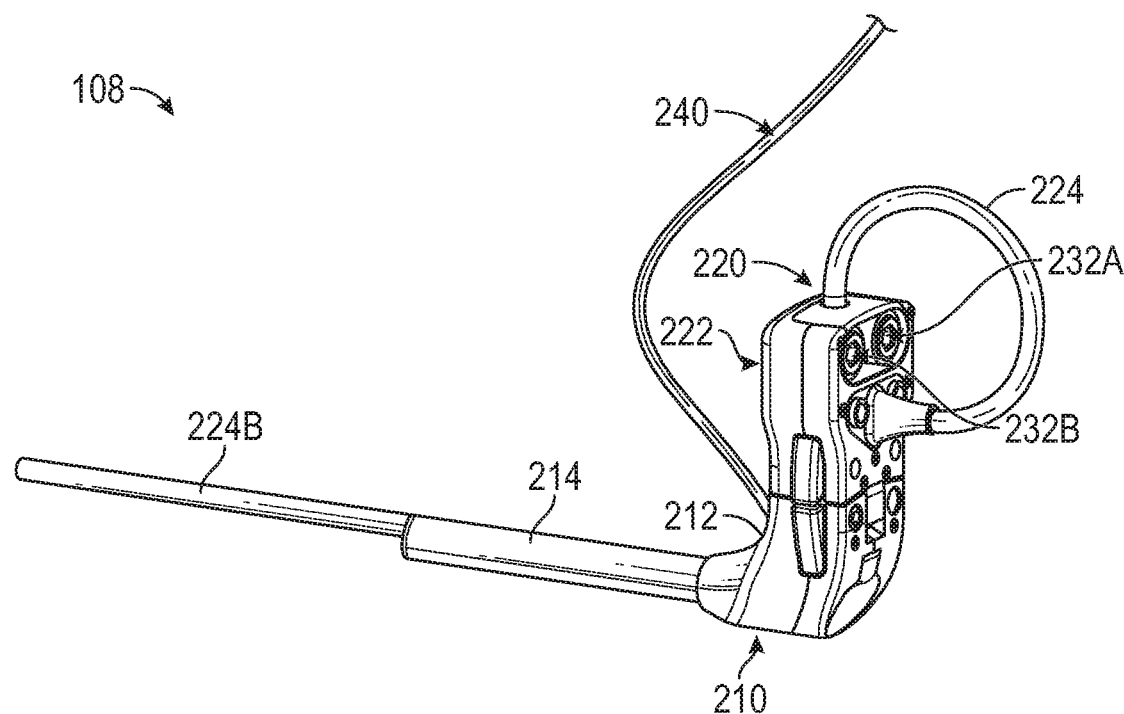
FIGS. 2A-2B illustrate insertion and visualization devices according to some embodiments.

Referring to FIG. 2A, in some embodiments, insertion and visualization devices 108 can include an insertion device 210 and a visualization device 220. The insertion device 210 can include a housing 212 and a plurality of passages, lumens, or channels 214 for inserting and guiding one or more instruments. The plurality of channels 214 can be enclosed in another housing. The two housings can be connected. As is illustrated, the plurality of channels, such as radial channels, can be formed within a housing, which can be radially shaped. The plurality of channels 214 can also permit insertion of a camera lumen, cable, elongate shaft, or tube 224. As is illustrated, a distal end 224B of the camera tube can extend beyond the housing including the plurality of channels 214. At least a portion of the distal end 224B can be positioned near or in the site of interest. One or more cameras can be positioned at the distal end 224B. The camera tube 224 can also include a proximal end 224A as described herein. In some embodiments, a channel of the plurality of channels 214 can house or support a camera in addition to or instead of the one or more cameras of the camera tube 224.

Figure 2B:
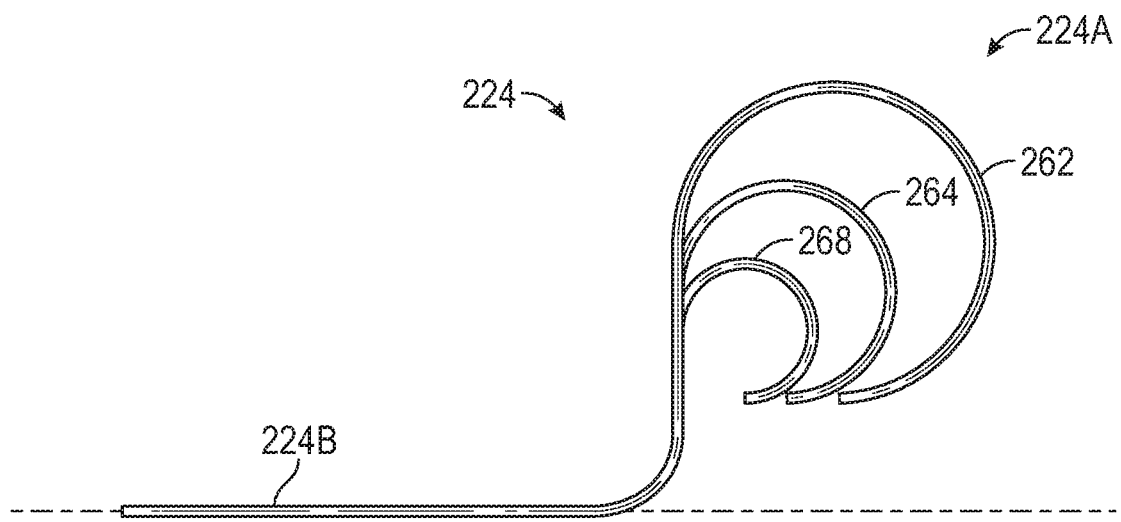

The visualization device can include a housing 222 to which the proximal end 224A of the camera tube can be removably (or non-removably) attached. The housing 222 can include an opening in which a one or more drivers, such as at least one of 232A or 232B, can be positioned. As described herein, the one or more drivers can move the camera tube 224 through the opening in the housing 222 and a channel of the plurality of channels 214 so that the distal end 224B extends away from one or more of the housings 212 or 222 or retracts back toward or into one or more of the housings 212 or 222. The camera tube 224 can form a loop around at least a portion of the housing 222 as illustrated in FIGS. 2A-2B. The diameter of the loop can be increased when the distal end 224B is retracted toward or into one or more of the housings 212 or 222 and be decreased when the distal end 224B is extended away from one or more of the housings 212 or 222. With reference to FIG. 2B, for example, when the distal end 224B is substantially fully retracted, the loop can have a diameter 262 as shown. When the distal end 224B is being extended away from the one or more of the housings 212 or 222, the diameter 264 of the loop decreases as compared to the diameter 264 of the loop. When the distal end 224B if fully extended away from the one or more of the housings 212 or 222, the diameter 268 of the loop can be smaller than the diameters 262 and 264. In some cases, extending the distal end 224B away from the one or more of the housings 212 or 222 causes the length of the proximal end 224A to decrease, which leads to a decrease in the diameter of the loop.

One or more cables 240 can be used to transmit control signals and data, such as analog or digital image data provided by the one or more cameras positioned at the distal end 224B or in the insertion device 210, to the patient cart 104. In some cases, transmission can be wireless and one or more cables 240 may not be present.

At least a portion of the camera tube 224 can be flexible or substantially flexible in order to form a loop and/or be guided through the one or more openings and/or channels are described herein. In some cases, looping the camera tube 224 upward around at least the portion of the housing 222 as described can permit the camera tube to have sufficient length for reaching near and/or into the site of interest, while eliminating or reducing the risk of the camera tube 224 coming into contact with non-sterile object, such as the floor.

Insertion Device

Figure 3A:
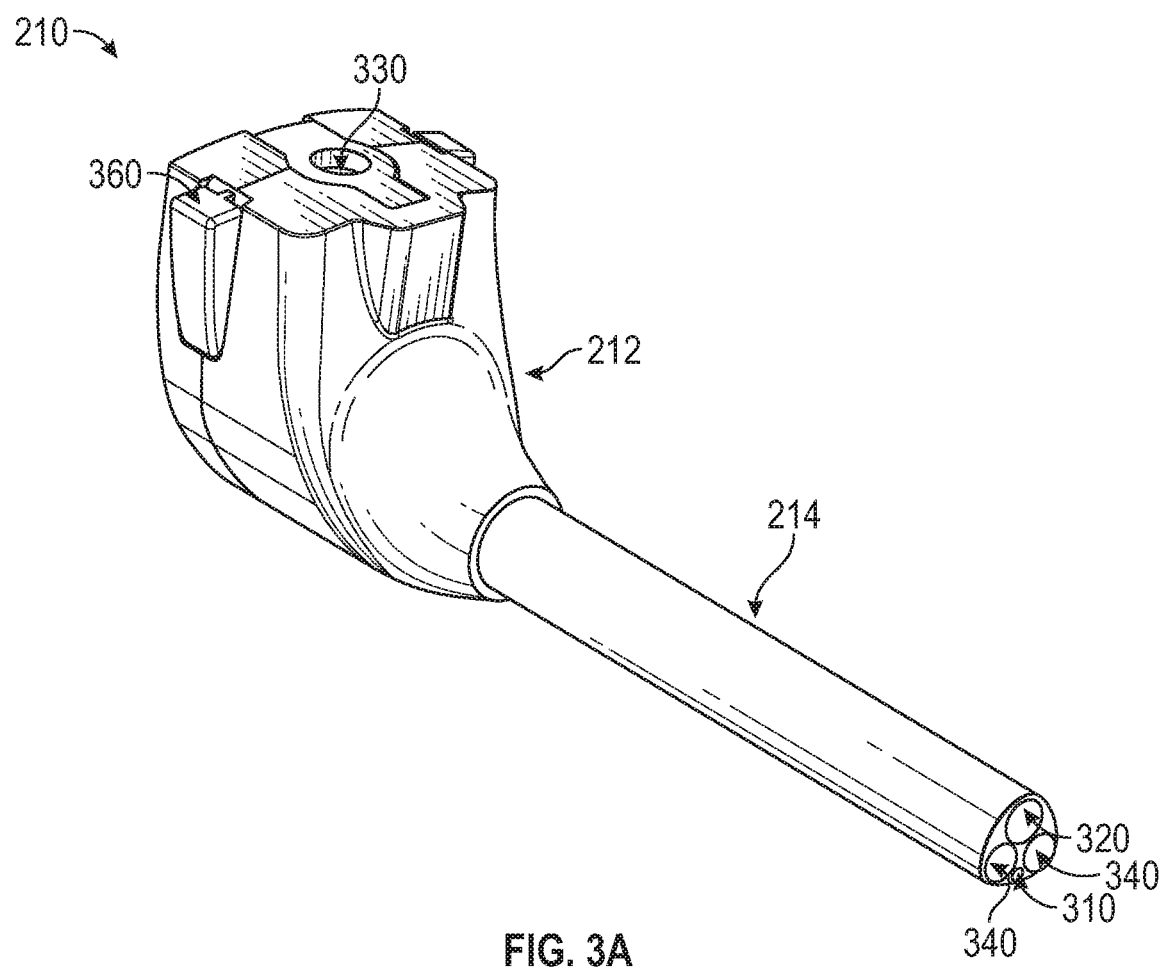

FIG. 3A illustrates a front perspective view of the insertion device 210 according to some embodiments. The housing 212 of the insertion device can include an opening 330 configured (for example, sized and/or shaped) to permit the camera tube 224 to pass through the housing 212. The opening 330 can include a seal, which may be covered by a closure (such as a latch), to prevent ingress of fluid, gas, or solids. Any of the seals described herein can include one or more valves, such as a duckbill valve. As illustrated in FIG. 3D showing a cross-section view of the insertion device 210, the housing 212 can include an interior passage 322 connecting the opening 330 to a channel 320 configured (for example, sized and/or shaped) to permit the camera tube 224 to pass through the channel. The interior passage 322 can be a channel positioned in an interior of the housing. The interior passage 322 can be bent or curved to facilitate various positional configurations of the visualization device 220 with respect to the insertion device 210 and in particular the housing 222 with respect to housing 212. The interior passage 322 can include an opening that aligns with or includes the opening 300 and another opening that aligns with or includes opening of the channel 320. In some cases, sealing material can be used on or around the interior passage 322 in addition to or instead of the seal in the opening 330. As illustrated in FIG. 2A, the distal end 224B of the camera tube 224 can exit the channel 320 and extend away from the insertion device 210 toward a site of interest, such as a surgical site, body cavity, wound, or the like. Also, the distal end 224B of the camera tube 224 can retract toward or into the channel 320 toward the insertion device 210 and away from the site of interest.

The plurality of channels 214 can include one or more instrument channels 340 configured (for example, sized and/or shaped) to permit one or more instruments to pass through and extend away from the insertion device 210 toward the site of interest. As is illustrated, there can be two channels for left and right instruments.

In some cases, the interior passage 322 includes at least a portion with a central axis parallel to a central axis of the one or more instrument channels 340. The interior passage 322 can include at least a portion (for example, the curved portion illustrated in FIG. 3D) with a central axis not parallel to a central axis of the one or more instrument channels 340.

The plurality of channels 214 can include a channel 310 for one or more cameras of the insertion device 210. In some implementations, a camera can be positioned at a distal end of the plurality of channels (or at or near position of the arrow 310). Such one or more cameras (which can be referred to as a secondary camera) can facilitate positioning adjacent to or insertion into the site of interest of at least one of one or more instruments or at least one of the one or more cameras of the visualization device 220 (such cameras can be referred to as a primary camera). The secondary camera can include a substantially flexible or substantially rigid lumen, cable, or elongate shaft that is inserted into the channel 310. The secondary camera can be integrated with the insertion device 210 or be removable. An opening of the channel 310 can include one or more seals, which may be covered by a closure (such as a latch), to prevent ingress of fluid, gas, or solids. In some cases, sealing material can be used on or around the opening of the channel 310 in addition to or instead of the seal(s) in the opening.

Figure 3C:
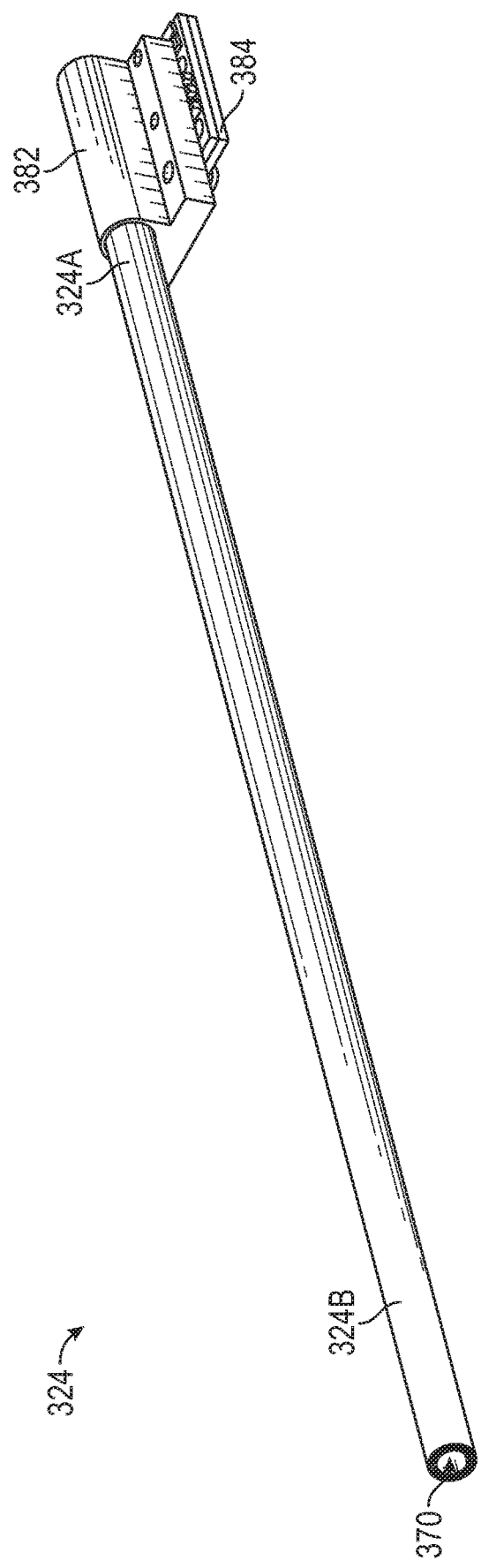
Figure 3D:
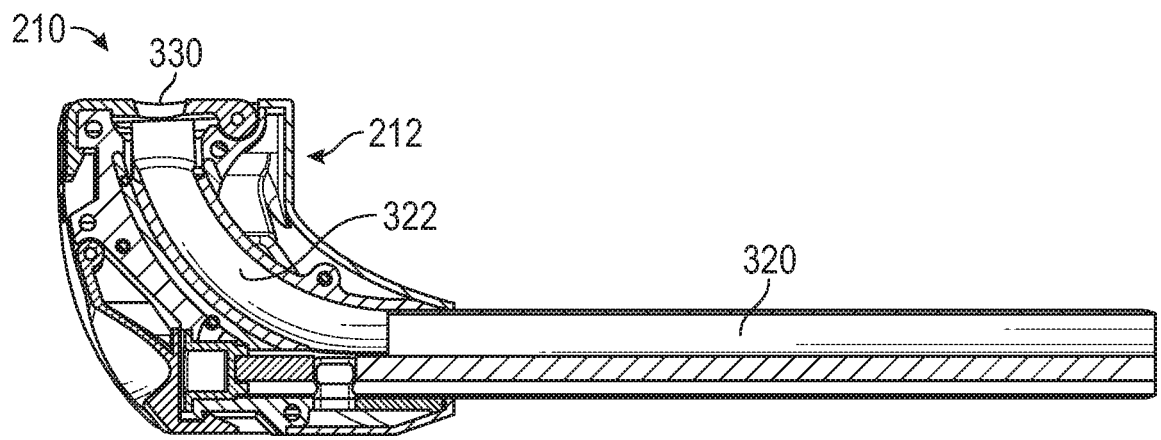

With reference to FIG. 3C, a secondary camera 324 can include a substantially flexible or rigid cable with a proximal end 324A and a distal end 324B. The distal end 324B can include a protector 370 (such as glass or plastic). The protector 370 can protect an imager and/or other components of the secondary camera breaking or malfunctions due to, for example, coming into contact with fluid in the site of interest. In other embodiments, a protector may be included as part of the insertion device 210 at a distal end of the channel 310, and accordingly the protector 370 may be optional. The secondary camera can include one or more lenses that focus light from and/or reflected by at least the portion of the site of interest on an image sensor 384. The image sensor can be positioned at the proximal end 324A and/or distal end 324B. The one or more lenses can include concave and/or convex lenses. In some cases, one or more lenses can be moved to adjust the zoom (such as, an optical zoom). The image sensor 384 can detect the light and convert it to image information or data. For instance, the image sensor 384 can measure brightness at a plurality of points. The image sensor 384 can include at least one of charge-coupled devices (CCDs), complementary metal-oxide-semiconductor (CMOS) image sensors, or the like. The image sensor 384 can be a digital and/or analog image sensor. In some implementations, the secondary camera can include two or more cameras (for example, to produce a stereoscopic image).

In some cases, the secondary camera 324 can include an optical system 382 that redirects the detected light. For example, the optical system 382 can be a prism that redirects the detected light down onto the image sensor 384. The image sensor 384 can be positioned in a different plane than a portion of the surgical site being imaged. The optical system 382 may be omitted in some implementations. For example, the optical system 382 may be omitted when the image sensor is positioned in the same plane as the surgical site being imaged.

The secondary camera 324 can be removable. For example, the secondary camera cable can be inserted into and/or removed from the channel 310. When the secondary camera cable is removed, the channel 310 can be used for one or more of suction or irrigation of the site of interest. The channel 310 can alternatively or additionally be used to permit an instrument (such as, third instrument) to be inserted. The instrument can be controlled by the robotic surgery system or manually by a user. A protector would not be included at a distal end of the channel 310 or would otherwise be removable when the channel 310 is used for one or more of aspiration, irrigation, instrument manipulation, or the like.

In some cases, the primary camera can be a stereo or stereoscopic camera, which can produce three-dimensional representation of at least a portion of the site of interest, and the secondary camera can be a two-dimensional camera. The secondary camera can have lower resolution than the primary camera. For example, the secondary camera can have 1920×1080 pixels (or 1080p) resolution. The primary camera can have resolution of 1080p, 4K, 8K, or the like. The channel 310 for the secondary camera can be smaller in size (such as, narrower or having smaller diameter) than the channel 320 for the primary camera. The secondary camera may also include an illumination device for illuminating the site of interest. The illumination device can be incorporated as part of the secondary camera such that the illumination device and a lens system of the secondary camera all fit within the diameter of the channel 310. In some cases, the illumination device may be an annular system with strands of fiber wrapping around a lens system for causing illumination to be provided to the site of interest using known means of fiber illumination.

In some cases, close proximity of the instrument channels 340 to one or more camera channels 310 or 320 can permit single port surgery.

The housing 212 can include one or more attachment mechanisms 360. For example, the one or more attachment mechanisms 360 can be buttons positioned on opposite sides of the housing 212. The buttons can be configured to removably attach the insertion device 210 to a mounting interface of the drive unit 106 (or, in some cases, additionally or alternatively to the housing 222 of the visualization device 220). Pushing the buttons can release the insertion device 210 from the mounting interface (and/or the housing 222 of the visualization device 220). The one or more attachment mechanisms 360 can permit attachment to and release of the insertion device 210 from supporting pins of the mounting interface (and/or the housing 222).

FIG. 3B illustrates a rear perspective view of the insertion device 210 according to some embodiments. Openings of the one or more instrument channels 340 can include one or more seals, which may be covered by a closure (such as a latch), to prevent ingress of fluid, gas, or solids. In some cases, sealing material can be used on or around at least one of the one or more openings of the one or more channels 340 in addition to or instead of the seal(s) in the one or more openings. The housing 212 can include one or more openings 350 for receiving one or more supporting rods of pins, which can be positioned on the mounting interface. The one or more attachment mechanisms 360 can permit attachment to and release of the insertion device 210 from the supporting pins (and/or from the visualization device 220). For example, the one or more attachment mechanisms 360 can activate or release a latch or lock, such as a cam lock, cam lock with a spring, or the like.

Visualization Device

Figure 4A:
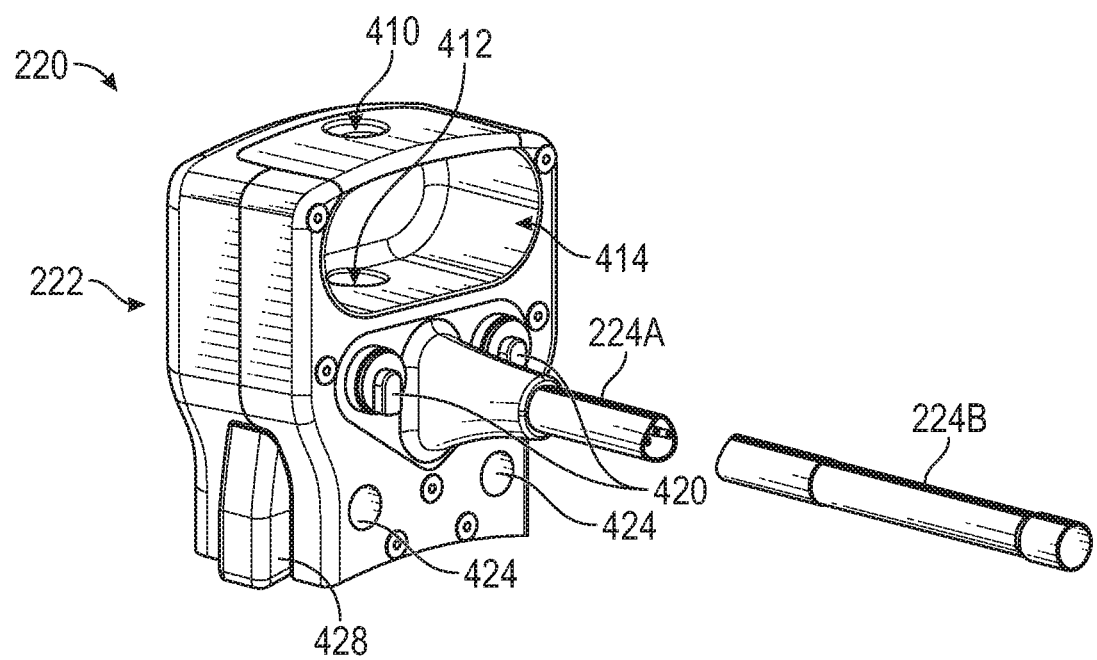
FIGS. 4A-4C illustrate a visualization device according to some embodiments.

FIG. 4A illustrates a front perspective view of the visualization device 220 according to some embodiments. The housing 222 of the visualization device can include openings 410 and 412 configured (for example, sized and/or shaped) to permit the camera tube 224 to pass through. As illustrated, the proximal end 224A of the camera tube 224 (illustrated for convenience without a middle portion) can be attached to the housing. The camera tube 224 can loop around at least the portion of the housing 222 when the distal end 224B is inserted through one or more of the openings 410 and 412 (see FIG. 2A). The openings 410 and 412 can be aligned to permit the camera tube 224 to pass through. A bottom opening (not illustrated) aligned with the opening 412 can be positioned on the bottom of the housing 222 to permit the camera tube 224 to exit the housing 222 after passing through an interior portion of the housing (such as, the interior portion illustrated in FIG. 4C). This bottom opening can be positioned adjacent to (such as over or on top of) the opening 330 in the housing of the insertion device 210 when the visualization device 220 is positioned adjacent to and/or attached to the insertion device. One or more of the openings 410, 412, or the bottom opening can include a seal, which may be covered by a closure (such as a latch) as described herein.

The housing 222 can include a drive opening 414. The drive opening can be positioned on a side of the housing 222 (for example, the back of the housing) that attaches to the mounting interface of the drive unit 106 as described herein. The drive opening 414 can be configured (for example, sized and/or shaped) to receive one or more drivers (at least one of 232A or 232B), such as a plurality of drive rollers as described herein (see, for example, FIG. 2A). With reference to FIG. 2A, the plurality of drive rollers can include right drive roller 232A and left drive roller 232B (collectively, referred to as 232). When inserted through the opening 410, the camera tube 224 is positioned between the right and left drive rollers 232A and 232B and contacts the drive rollers. The drive rollers 232 can contact, grip, or abut the camera tube 224. The drive rollers can advance the camera tube 224 down or retract it up through the drive opening 414. Movement of the drive rollers 232 in a first direction can advance the camera tube 224 forward or down through the drive opening 414 in order to advance the distal end 224B toward the site of interest. For example, the right driver roller 232A can spin counterclockwise and the left drive roller 232B can spin clockwise in order to advance the camera tube 224 forward. Such combination of the counterclockwise and clockwise movement of the drive rollers can constitute the first direction. Movement of the drive rollers 232 in a second direction can retract the camera tube 224 backward or up through the drive opening 414 in order to retract the distal end 224B away from the site of interest. For example, the right drive roller 232A can spin clockwise and the left drive roller 232B can spin counterclockwise in order to retract the camera tube 224 backward. Such combination of the clockwise and counterclockwise movement of the drive rollers can constitute the first direction. For each of the right and left drive rollers, movement in the second direction can be opposite to movement in the first direction even in cases where drive rollers spin in opposite directions during movement in the first and/or section direction.

Drive rollers 232 can have an external surface that is made out of and/or is covered by soft material, such as rubber, foam, or the like, that grips an external surface of the camera tube 224 in order to one or more of advance or retract the camera tube. In some embodiments, a portion of the camera tube 224 positioned between the drive rollers 232 can slip along the drive rollers, and as a result the camera tube would not be advanced or retracted. For example, slipping can be advantageous when a user's limb becomes caught in the loop formed by the camera tube 224 or in case of malfunction to prevent or lessen the risk of injury to the user or damage to one or more of the camera tube 224, the visualization device 220, the insertion device 210, or any other part of the system 100. At least one of one or more of the material on the external surface of the drive rollers 232 or on an external surface of the camera tube 224 or a surface pattern on the surface of one or more of the external surface of the drive rollers 232 or the external surface of the camera tube 224 can be selected to have a friction coefficient that results in slippage in case force on the camera tube exceeds a maximum force, such as, a maximum frictional force. The maximum frictional force can depend on one or more of the friction coefficient between the drive rollers 232 and camera tube 224 or a clamping force between the drive rollers 232 and camera tube 224. In some cases, the maximum frictional force can be 5N or less or more, 7N or less or more, 10N or less or more, or the like. Surface pattern on the external surface of the drive rollers 232 (and/or the external surface of the camera tube 224) can affect the friction coefficient. For example, ribbed surface pattern, toothed surface pattern, or the like can increase the friction coefficient compared to a smooth or substantially smooth surface pattern.

At least a portion of the distal end 224B of the camera tube 224 can articulate to permit viewing of at least a portion of the site of interest. The housing 222 can include one or more actuators 420 configured to control movement of the distal end 224B of the camera tube 224, which can include one or more cameras. In some cases, a first actuator can control pitch or tilt (up/down movement) of the distal end 224B, and a second actuator can control yaw or pan (left/right movement) of the distal end 224B. The first and second actuators can control movement of the distal end 224B by manipulating links positioned in the interior of the camera tube 224 as described herein (for example, with reference to FIGS. 4B-4C).

The housing 222 can include one or more attachment mechanisms 428. For example, the one or more attachment mechanisms 428 can be buttons positioned on opposite sides of the housing 222. The buttons can be configured to removably attach the visualization device 220 to the mounting interface of the drive unit 106 (or, in some cases, additionally or alternatively to the housing 212 of the insertion device 210). Pushing the buttons can release the insertion device 210 from the mounting interface (and/or the housing 212). The one or more attachment mechanisms 428 can permit attachment to and release of the visualization device 220 from one or more supporting rods or pins (and/or the housing 212). As described herein, the one or more attachment mechanisms 428 can activate or release a lock, such as a cam lock, cam lock with spring, or the like. The housing 222 can include one or more openings 424 for receiving one or more the supporting pins that can be positioned on the mounting interface.

Figure 4B:
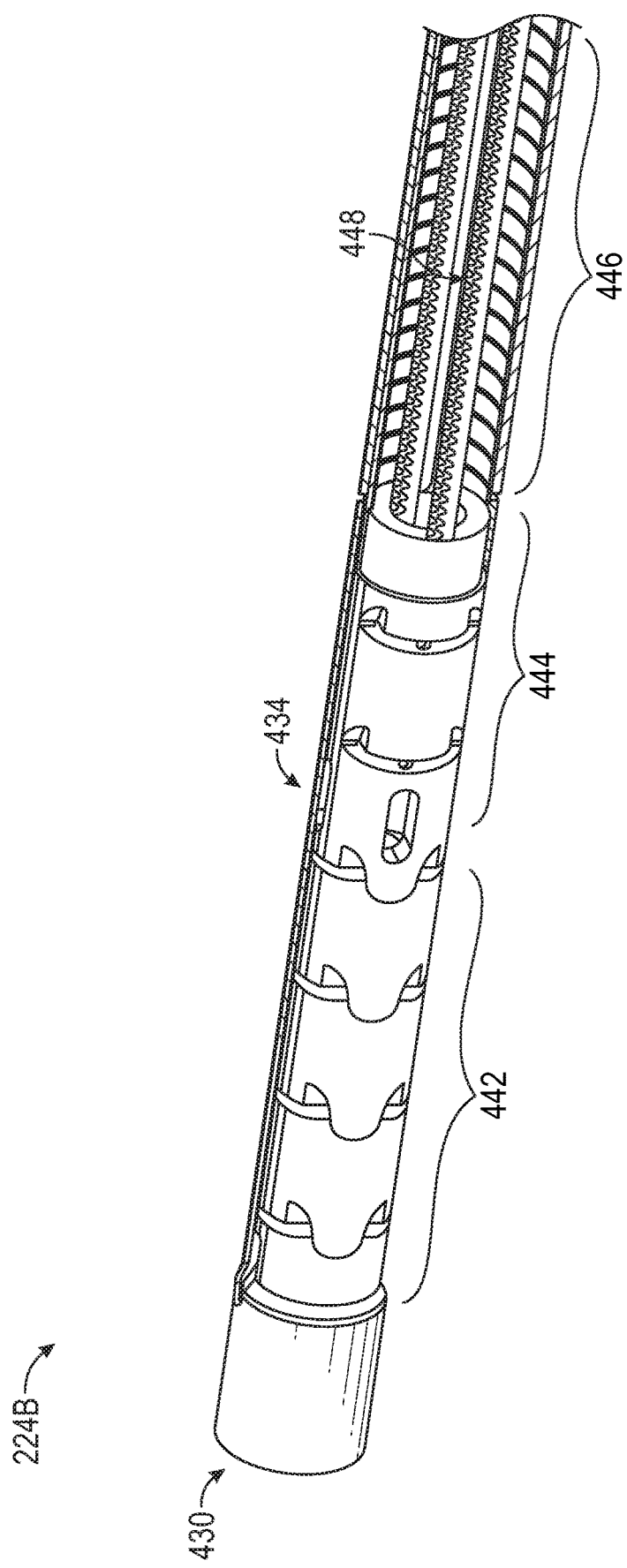

FIG. 4B illustrates a perspective view of the distal end 224B of the camera tube 224 according to some embodiments. An imager 430 (which can be the primary camera) with one or more cameras can be positioned at or near the tip of the distal end 224B. The distal end 224B can include a pitch or tilt segment or section 442 for controlling up/down movement of the distal end 224B, and a yaw or pan segment section 444 for controlling left/right movement of the distal end 224B. As illustrated, the tilt section 442 can be positioned adjacent the imager 430, and the pan section 444 can be positioned adjacent to the tilt section. Pan section 444 can be positioned farther away from the tip of the distal end 224B than the tilt section 442. In some cases, positioning of the sections 442 and 444 relative to the tip can be reversed. In some cases, the sections 442 and 444 can be intermingled with respective couplings or guides (as described below) of the sections 442 and 444 alternating.

At least one of sections 442 or 444 can include one or more couplings or guides 434. The one or more couplings 434 can be coupled to each other to allow bending of the distal end 224B. The sections 442 and 444 can bend (as described herein) as a result of at least one of pulling or pushing one or more flexible or substantially flexible links 448 positioned in the interior of the camera tube 224 that control, for example, the bend, curvature, or another aspect of spatial orientation of one or more of sections 442 or 444. One or more links 448 can include a wire, cable, or the like with elasticity that can support at least one of tension or compression without permanent deformation. One or more links 448 can be connected to the one or more guides 434 (for example, by being connected to the one or more guides in the interior of the camera tube 224). Movement, such as pulling and/or pushing, of the one or more links 448 can cause adjustment of the spatial orientation of the one or more guides 434 and, as a result, one or more sections 442 or 444.

As described herein, one or more actuators 420 can pull and/or push the one or more links 448, for example, via rotation in first and/or second directions. Pulling a link 448 can cause shortening its length, while pushing the link can cause lengthening the link (such as, returning the link substantially to its initial length).

Segment or section 446 can be positioned adjacent the pan section 444 at the distal end 224B of the camera tube 224. As described herein, section 446 can be flexible or substantially flexible. One or more of sections 442 or 444 can be rigid or substantially rigid to prevent at least the imager 430 of the distal end 224B from drooping or sagging as the distal end 224B exits the channel 320 of the insertion device. Drooping or sagging can undesirably lead to at least a temporary loss of vision of at least a part of the site of interest or inadvertent contact with tissue near or outside the site of interest. Rigidity of the one or more sections 442 or 444 can prevent movement of the distal end 224B in a downward direction (for example, in the absence of actively tilting the camera tube 224 as described herein), while permitting movement in the opposite direction as the camera tube 224 is passed through one or more openings or channels, as described herein. Rigidity can help maintain orientation of at least the imager 430 in same plane of the channel 320 or in a plane above the plane of the channel 320 as the distal end 224B of the camera tube 224 exits the channel 320. The latter plane can be parallel or substantially parallel to the plane of the channel 320.

In some cases, to increase the rigidity of the distal end 224B, a supporting material or mechanism may be added to the distal end 224B to help maintain orientation of at least the imager 430 in the same plane of the channel 320. Such design can prevent the camera from drooping and/or contacting unwanted areas of the site of interest. The supporting material or mechanism can allow the distal end 224B to flex (or curve) in one direction in a plane while preventing other flexing (or curving), thereby allowing the distal end 224B to move through a curved portion of the interior passage 322 of the housing 212. With reference to FIG. 3D, for instance, flexing in the direction of the bend or curve of the interior passage 322 can be permitted, while flexing in the other direction may not be permitted.

Figure 4C:
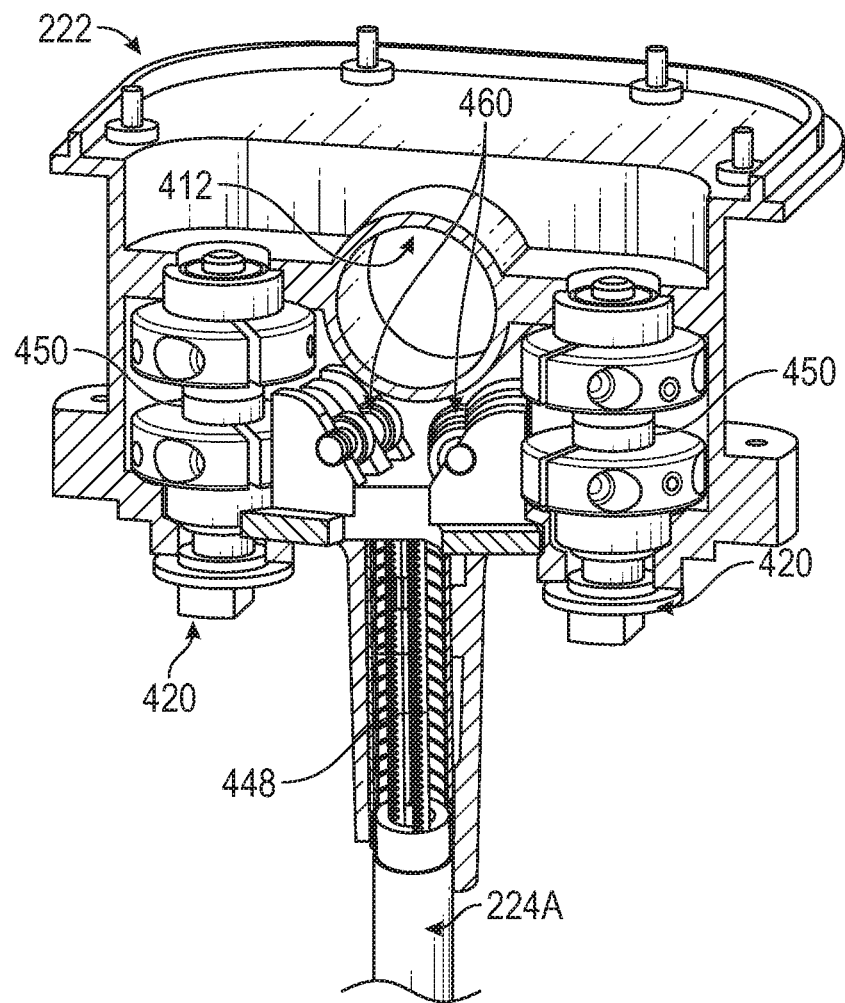

FIG. 4C illustrates a cross-sectional view of the housing 222 and camera tube 224 of the visualization device 220 according to some embodiments. The figure depicts view of an interior portion of the housing 222 looking up through the opening 412 in the housing 222. Proximal end 224A of the camera tube 224 can be attached to the housing 222 as described herein. As illustrated, interior of the proximal end 224A can include one or more links 448 that extend along the length of the camera tube 224 to the distal end 224B, as described herein. In use, the camera tube 224 passes through the interior portion illustrated in FIG. 4C.

The one or more actuators 420 can include first and second actuators that, respectively, control tilting or panning of the distal end 224B of the camera tube 224. For example, the first actuator can control pulling and/or pushing of one or more links 448 connected to a plurality of guides in the tilt section 442. The first actuator can control tilting up/down of at least the imager 430. The second actuator can control pulling and/or pushing of one or more links 448 connected to a plurality of guides in the pan section 444. The second actuator can control left/right movement of at least one of the tilt section 442 and/or the imager 430.

Pulling and/or pushing at least one link 448 can be performed via actuating the first and/or second actuator 420. With reference to the first actuator, for instance, its exterior portion that protrudes from the housing 222 can serve as a shaft connected to a drum 450 located in the interior of the housing 222. Rotation of the shaft and drum can cause a corresponding link pulley 460 to rotate, for example, in a plane perpendicular to the plan of rotation of the shaft and drum. The pulley 460 can be connected to the drum 450 such that rotation of the drum causes the pulley to rotate. The drum 450 can have threading on the surface that contact threading on the surface of the pulley 460 and transfers rotation to the pulley. The pulley 460 can be connected to at least one link 448. For instance, the at least one link can be attached to the pulley. Rotation of the actuator 420 in a first direction (for example, clockwise) can cause rotation of the corresponding shaft (for example, in the same clockwise direction). This can cause the corresponding pulley 460 to rotate and, for instance, pull (or push) the associated at least one link, which can cause tilting of at least the imager 430. In some cases, the pulley 460 can be connected to a pair of links 448 one of which is pulled while the other is pushed to control the tilting. Second actuator can operate similarly to control the panning.

Additional details of controlling one or more of the tilt or pan of the distal end 224B of the camera tube are similar to those described in U.S. Patent Publication No. 2016/0143633 and U.S. Pat. No. 9,629,688, which are assigned to the assignee of the present application and the disclosure of each of which is incorporated by reference in its entirety.

Mounting Interface and Sterile Barrier

Figure 5A:
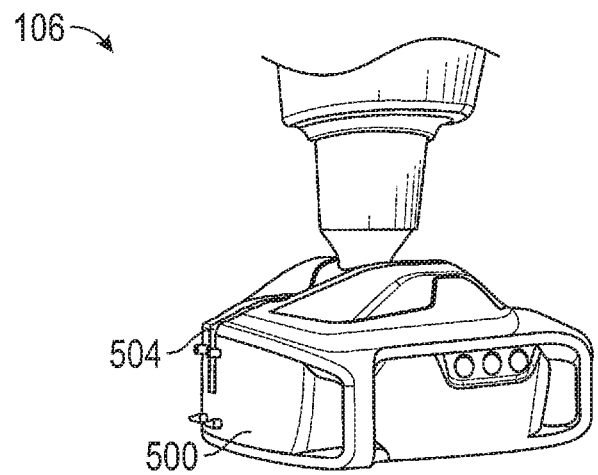
FIGS. 5A-5E illustrate a mounting interface of a drive unit of a robotic surgery system according to some embodiments.

FIG. 5A illustrates the drive unit 106 of the robotic surgery system 100 according to some embodiments. The drive unit 106 can include a mounting interface 500 configured to support one or more of the insertion device 210 or visualization device 220. The mounting interface can include an opening or slit 504 for receiving a looped portion of the camera tube 224 (see, for example, FIG. 6I).

Figure 5B:
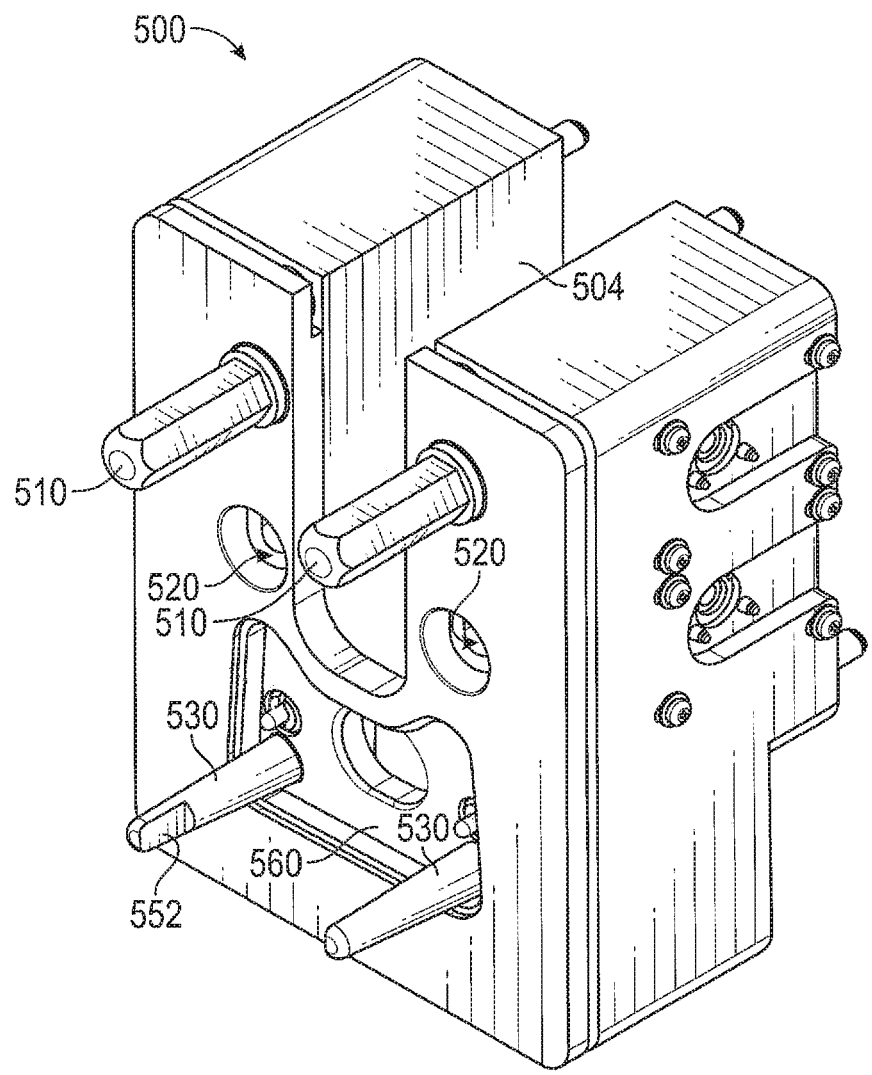

FIG. 5B illustrates a perspective view of the mounting interface 500 according to some embodiments. The mounting interface 500 can include one or more posts or pins 510 configured to actuate one or more drivers 232 for moving the camera tube 224 as described herein. As illustrated, the pins 510 can be provided to support the rollers 232A and 232B. The pins 510 can be configured (for example, sized and/or shaped) to attach to the rollers 232A and 232B. For example, the pins 510 can be hexagonal, and the rollers 232A and 232B can include hexagonal openings (see, for example, FIG. 5D) configured (for example, sized and/or shaped) to be mounted on the hexagonal surface of the pins 510. In some cases, one or more shapes such as square, round, triangular, or the like can be used in addition to or instead of hexagonal.

The mounting interface 500 can include one or more actuators 520 for causing movement of the one or more actuators 420 of the visualization device 220. As illustrated, two actuators 520 can be provided, and they can include shafts or recesses configured (for example, sized and/or shaped) to receive protruding exterior portions of the actuators 420. Within the recesses, the actuators 520 can include surfaces configured (for example, sized and/or shaped) to mate with the surfaces of the protruding exterior portions of the actuators 420. The mating can provide attachment of the actuators 420 of the visualization device 220 to the actuators 520 of the mounting interface 500.

As described herein, the mounting interface 500 can support one or more of the insertion device 210 or visualization device 220. As illustrated in FIG. 5B, the visualization device 220 can be at least partially supported by the pins 510 supporting the drivers 232 that are placed in the recess 414 of the housing 222. The mounting interface 500 can include one or more pins 530 configured to support the insertion device 210. The one or more pins 530 can be configured (for example, sized and/or shaped) to be received in the one or more openings 350 of the insertion device 210. The one or more pins can have size, shape, and/or surface pattern configured to be attached to insertion device 210. For example, as is illustrated, a left pin 530 can have a groove, pattern, or indentation 552 at or near its tip. The indentation 552 can be configured (for example, sized and/or shaped) to mate with a surface in the interior of the left opening 350 (see, for example, FIG. 3B. This can provide attachment of the insertion device 210 to the mounting interface 500. As described herein, one or more attachment mechanisms 360 can operate to disengage the visualization device 210 from the mounting interface 500. For example, one or more attachment mechanisms 360 can be pressed to disengage mating of the surface in the interior of the left opening 350 with the indentation 552. The right pin 530 can have a similar groove, pattern, or indentation 552 at its tip on the side facing the left pin.

Figure 5C:
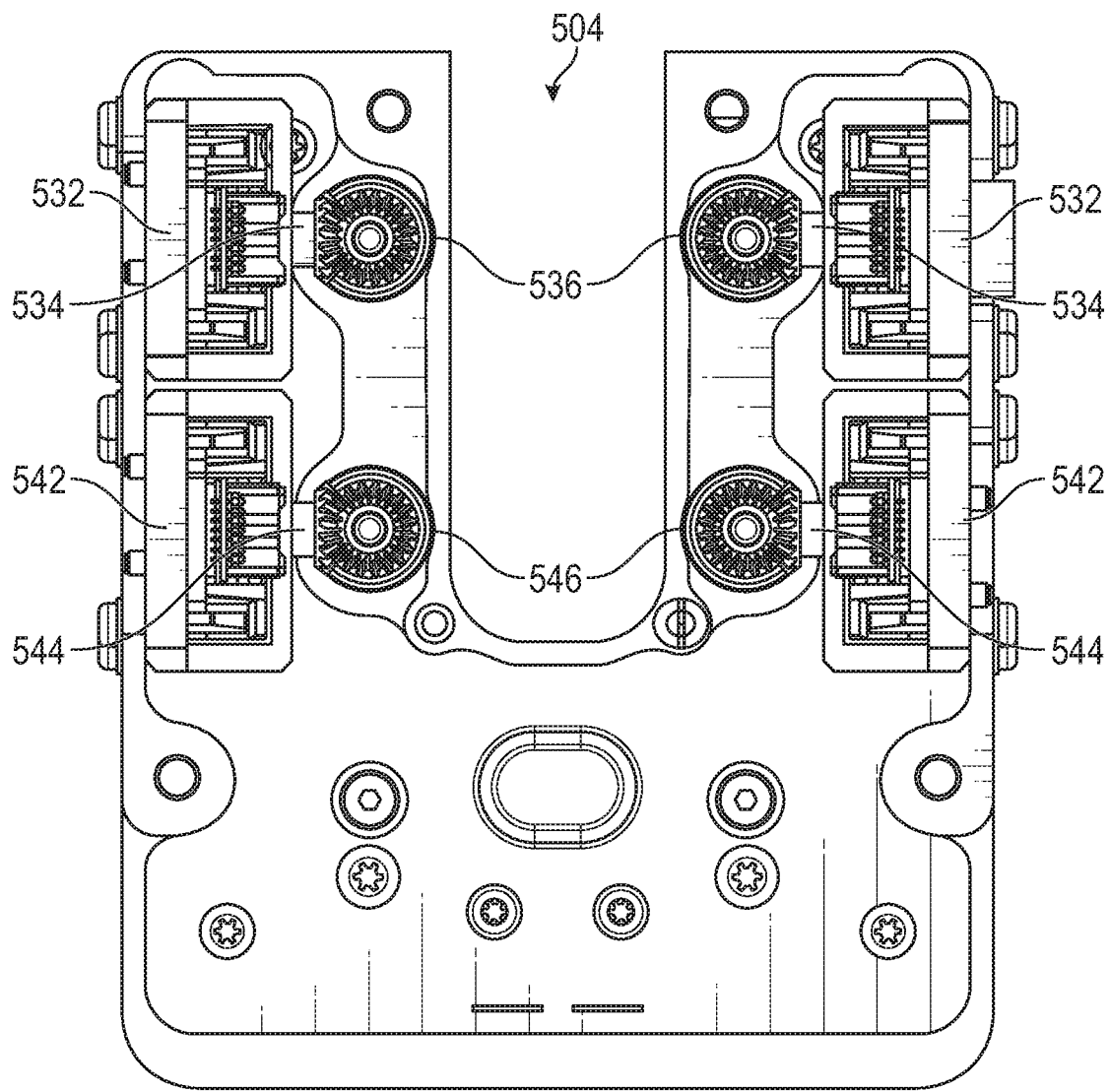

FIG. 5C illustrates a rear view of the mounting interface 500 according to some embodiments. The mounting interface can include a first set of actuators 532, a first set of gears 534 connected to or attached to the first set of actuators 532, and a second set of gears 536 cooperating with the first set of gears 534. These components can be collectively configured to actuate the one or more pins 510. As illustrated, the first set of actuators 532 can include two actuators, the first set of gears 534 can include two gears, and the second set of gears 536 can include two gears. In some cases, the first set of actuators can be motors, for example, electric motors.

The first set of gears 534 can interlock with the second set of gears 536. In some cases, the first set of actuators 532 can be configured to rotate the first set of gears 534 attached to the first set of actuators 532. Rotation of the first set of gears 534 can cause the second set of gears 536 to rotate in a plane perpendicular to the plane of rotation of the first set of gears 534. The one or more pins 510 can be connected or attached to the second set of gears 536. Rotation of the second set of gears 536 can cause rotation of the one or more pins 510. Rotation of the one or more pins 510 can cause rotation of the one or more drivers 232 and movement of the camera tube 224, as described herein. Rotation of the one or more pins 510 and one or more drivers 232 can be in the first and/or second direction to advance and/or retract the camera tube 224, as described herein. Rotation in the first and/or second direction can be caused by movement of the one or more actuators in at least two directions (for example, clockwise or counterclockwise).

The mounting interface 500 can include a second set of actuators 542, a third set of gears 544 connected to or attached to the second set of actuators 542, and a fourth set of gears 546 cooperating with the third set of gears 544. Collectively these components can be configured to actuate the one or more actuators 520. As illustrated, the second set of actuators 542 can include two actuators, the third set of gears 544 can include two gears, and the fourth set of gears 546 can include two gears. In some cases, the first set of actuators can be motors, for example, electric motors.

The second set of actuators 542, third set of gears 544, and fourth set of gears 546 can cooperate with each other and operate to actuate the one or more actuators 520 similarly to the foregoing description of actuating the one or more pins 510. As described herein, movement of the actuators 520 and corresponding movement of the actuators 420 of the visualization device 220 can cause the camera tube 224 to tilt and/or pan.

Figure 5D:
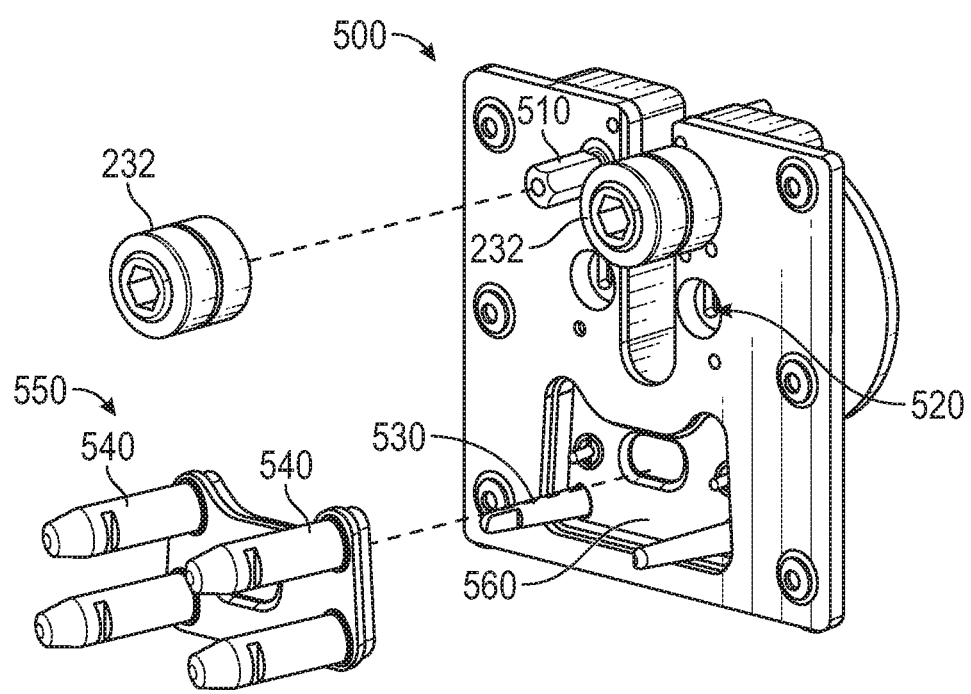

FIG. 5D illustrates the mounting interface 500 prepared for supporting one or more of the insertion device 210 or visualization device 220 according to some embodiments. In some implementations, a sterile barrier may need to be provided between the mounting interface 500 of non-sterile drive unit 106 and the insertion device 210 and/or sterile visualization device 220. The insertion and visualization devices, 210 and 220, may be required to be sterile in order to protect the site of interest from infection in case of one or more of the insertion or visualization device coming into contact with the site of interest or with another sterile component of the system 100 (such as, an instrument) that may come into contact with the site of interest, with a user performing or assisting with the surgery.

One or more drivers 232 (for example, rollers) can be sterile and can be attached to or mounted on the one or more pins 510 of non-sterile mounting interface 500. A sterile cover 550 can be attached to or mounted to cover the one or more pins 530. With reference to FIG. 5B, the cover 550 can be mounted in a region 560 on a front surface of the mounting interface 500. The cover 550 can be secured with one or more closures (not illustrated). For example, the one or more closures can be pins that are pushed in by the cover 550 when it is mounted in the region 560. Pushing of the pins can cause a closure, such as a latch, to become closed. The cover 550 can be removed from the region 560, for example, by pressing a button positioned on the bottom surface of the mounting interface 500 (not shown), which can push the pins against the cover 550 and dislodge the cover.

The cover 550 can include a bottom set of pin covers for covering the one or more pins 530. The cover 550 can include a top set of pins 540 that can be configured to support the visualization device 220 when it is attached to the mounting interface 500. The set of pins 540 can be sized and/or shaped to be received in the one or more openings 424 of the visualization device 220. The set of pins 540 can have size, shape, and/or surface shape configured to be attached to the visualization device 220, for example, as described herein in connection with the pins 530.

Figure 5E:
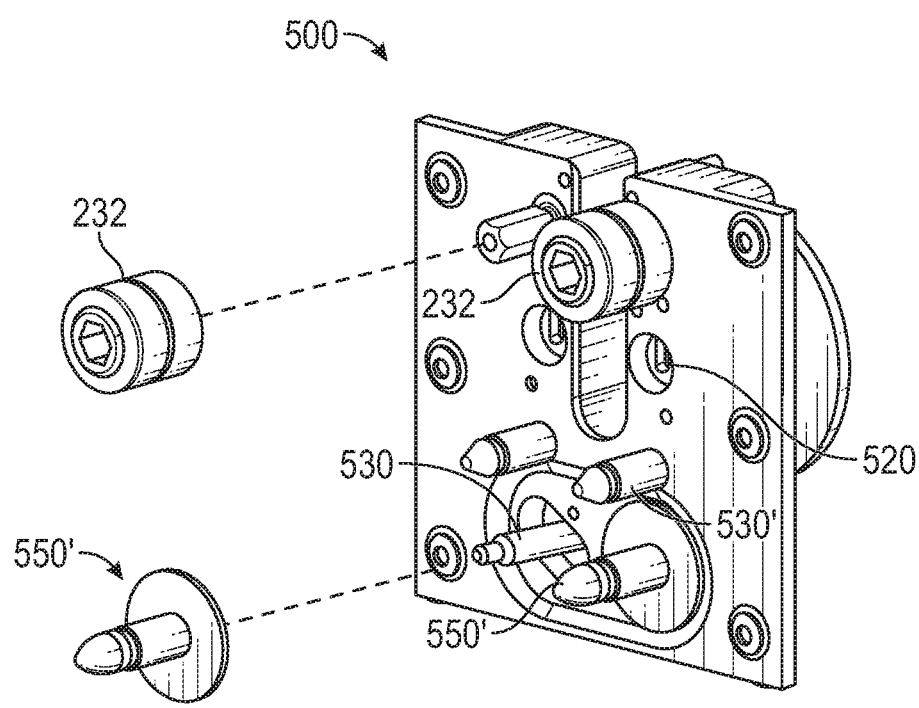

With reference to FIG. 5E, in some implementations, the mounting interface 500 can include one or more pins 530' configured (for example, sized and/or shaped) to support the visualization device 220. For example, the one or more pins 530' can function similar to the one or more pins 540. One or more pins 530' can be covered by the cover 550, such as by pin covers 540. In some cases, as illustrated in FIG. 5E, individual covers 550' can be used to cover each of the one or more pins 530 and/or 430'. In some embodiments, two separate covers can be used to cover the one or more pins 530 and 430' respectively. In some implementations, a single cover 550 (as illustrated in FIG. 5D) but with pin covers replacing the top set of pins 540 can be used to cover the one or more pins 530 and 530'.

In some cases, a sterile barrier can be formed between one or more actuators 420 of the visualization device (see, for example, FIG. 4A) and one or more actuators 520 of the mounting interface (see for example, FIG. 5B) in one or more of the following ways. One or more actuators 420 can be covered by one or more sterile covers as described herein. A sterile drape can be placed over the drive unit 106 and the mounting interface. Drape material can flex and/or slip to provide the sterile barrier. Drape material can have appropriate thickness and/or other properties to allow for the flexing and/or slippage. The drape can include one or more sterile covers (which can function as actuators) that transfer motion between the one or more actuators 420 and one or more actuators 520. The one or more sterile covers can be embedded or integrated into the drape.

The one or more drivers 232 and one or more covers 550 can serve as at least a partial sterile barrier between the mounting interface 500 and the insertion and visualization devices and the camera tube 224. Any one or more of the drivers 232, one or more of the covers 550, or any other sterile barriers disclosed herein can be disposable or can be reused after being sterilized. For example, the one or more sterile covers 550 can be made out of plastic and be disposable. As another example, rollers 232A and 232B can be disposable.

Any of the sterile components described herein can be sterilized by fluid or gas (such as ethylene oxide (EtO)), heat (such as autoclaving), irradiation (such as gamma irradiation), or the like. For example, the one or more openings in the insertion device 210 and/or visualization device 220 can facilitate fluid or gas to contact exterior and interior surfaces during sterilization.

Docking the Insertion and Visualization Devices

FIG. 6A illustrates the insertion device 210, visualization device 220, one or more covers 550, drivers (such as rollers) 232A and 232B, and the mounting interface 500 of the drive unit 106 according to some embodiments. As illustrated in FIG. 6B, a sterile drape 600 can be placed over drive unit 106 (and, in some cases, other parts of the robotic surgery system) to provide additional or alternative sterile barrier. For example, the drape 600 can act as a sterile barrier permitting a user performing or assisting with the surgery to touch the drive unit 106. One or more holes 610 can be made in the drape 600 to permit one or more pins 510, 530, and/or 540 or 530' to be accessed. Positions and sizes of the one or more holes 610 can correspond to positions and sizes of the one or more pins. The drape 600 can be pulled tight around the drive unit 106 and other components of the system 100 as illustrated in FIG. 6C. The drape 600 can be held in place with one or more of ties, adhesive attachments, magnetic attachments, or the like.

Figure 6D:
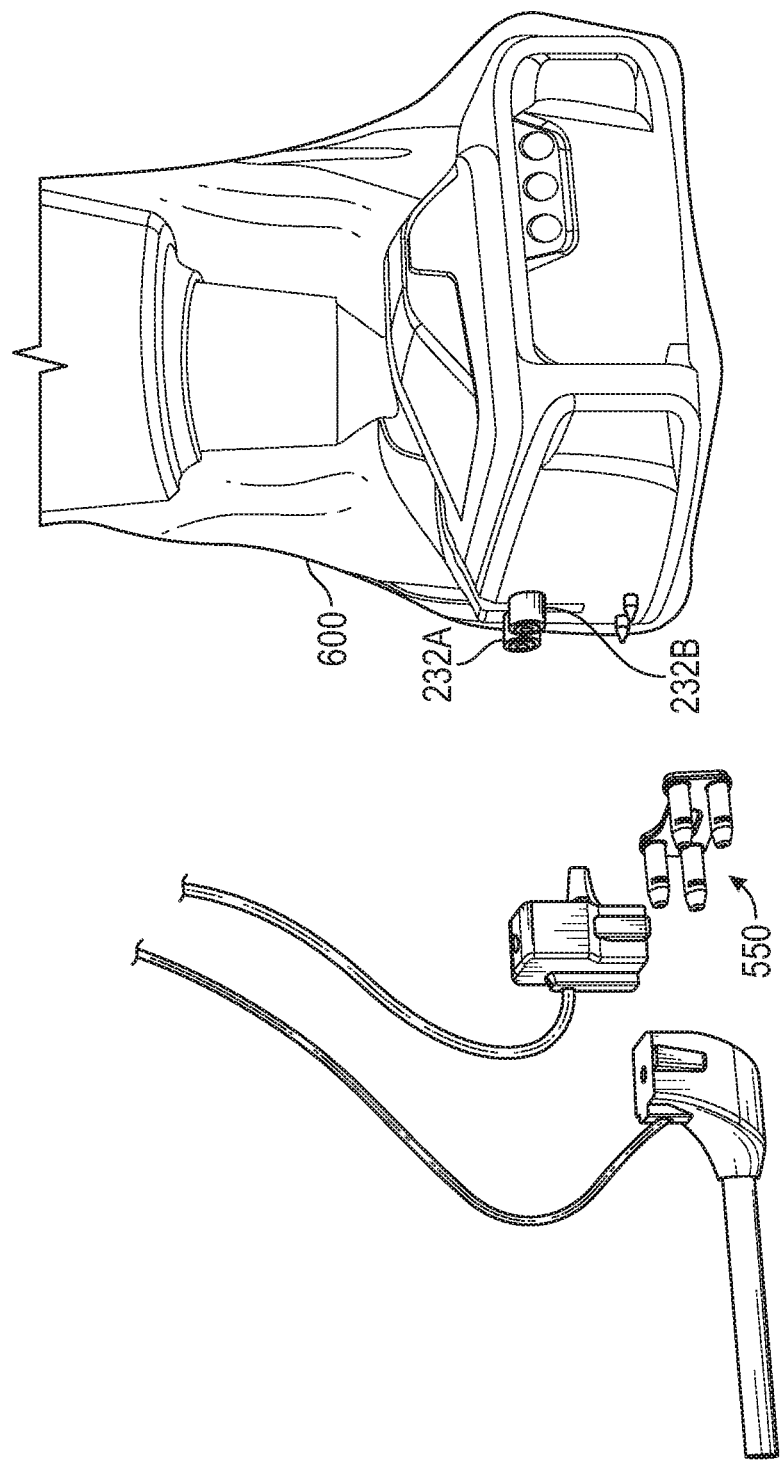
Figure 6E:
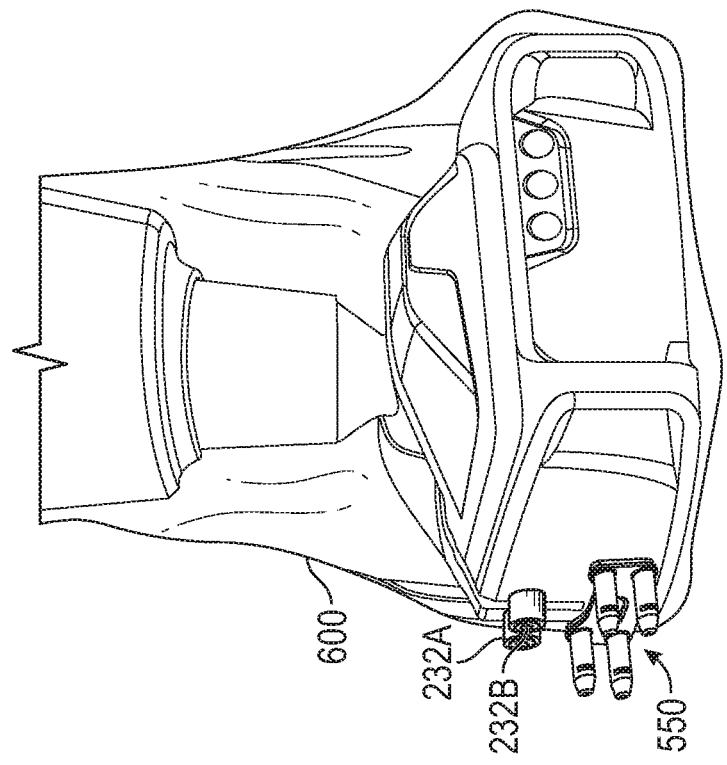
Figure 6E:
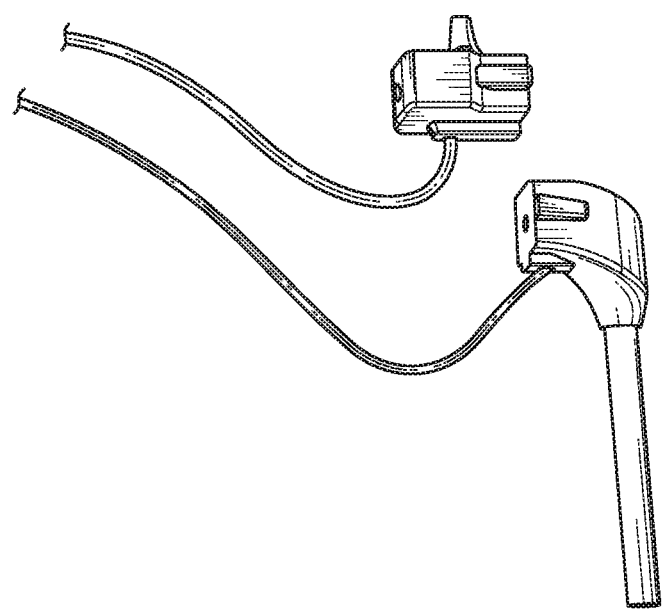

The drivers 232A and 232B can be mounted on the one or more pins 510 as illustrated in FIG. 6D and described herein. The one or more pins 510 can be exposed through corresponding one or more holes 610 in the drape 600. One or more covers 550 can be mounted on one or more pins 530 and/or 530' as illustrated in FIG. 6E and described herein. The one or more pins 530 and/or 530' can be exposed through corresponding one or more holes 610 in the drape 600.

Figure 6F:
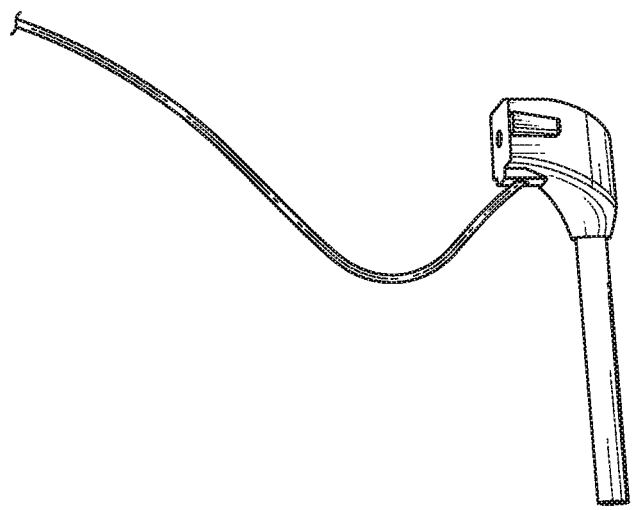
Figure 6F:
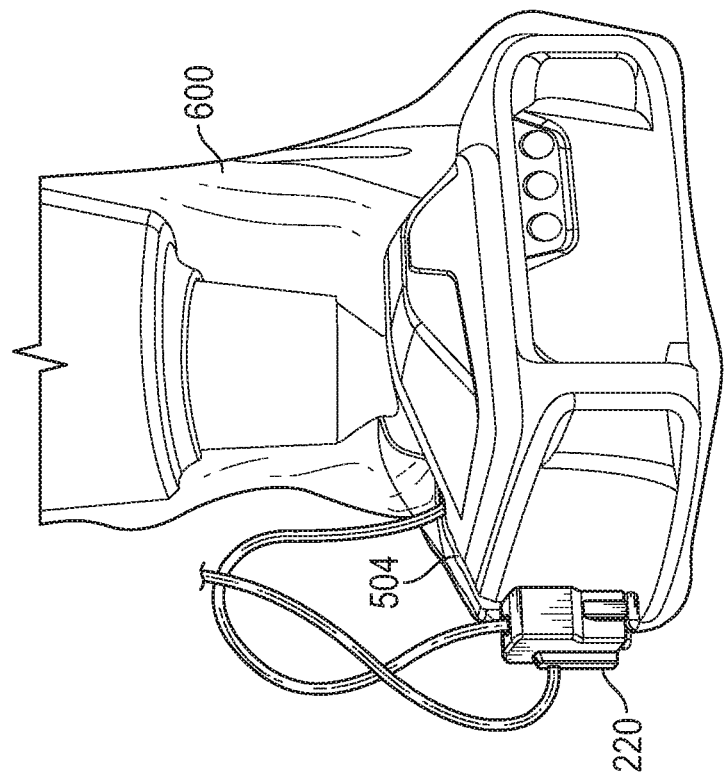

The visualization device 220 can be mounted on (or docked to) the mounting interface 500 as illustrated in FIG. 6F and described herein. The camera tube 224 (which can be sterile) can be inserted into the visualization device 220 as described herein. At least a portion of the loop of the camera tube 224 can be positioned in the slit 504 as shown. The drape 600 can include enough slack to allow the camera tube 224 and surrounding drape material to be placed in the slit 504. In some cases, the drape 600 can include a portion shaped to generally correspond with the slit 504 to facilitate positioning of the portion of the loop of the camera tube 224 in the slit 504.

Figure 6G:
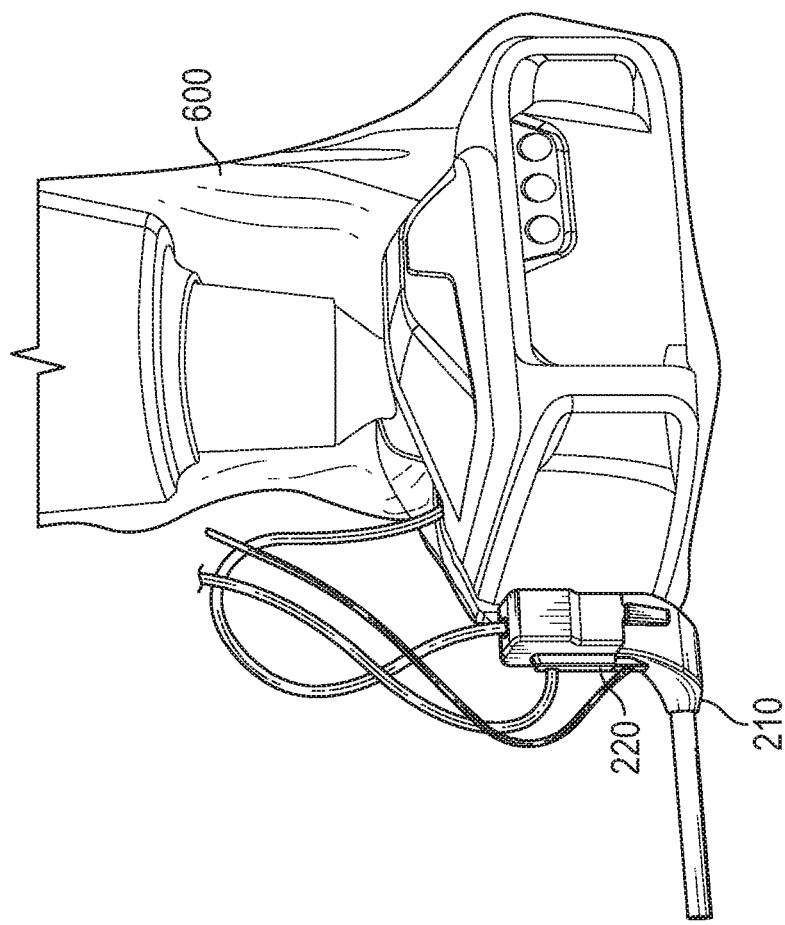

The insertion device 210 can be mounted on (or docked to) the mounting interface 500 as illustrated in FIG. 6G and described herein. In some cases, the insertion device 210 may have already been placed near or into the site of interest prior to being mounted on the mounting interface 500. In such cases, the drive unit 106 can be brought toward the insertion device 210 for docking the insertion device. The order of the mountings (or connections or dockings) can be interchanged. For example, the visualization device 220 can be mounted on the mounting interface 500 after the drive unit 106 has been docked with the insertion device 210. The visualization device 220 and insertion device 210 can be independent from each other (for example, modular) so that the visualization device 220 can be changed during surgery if it breaks down or otherwise becomes unresponsive without the need to first undock the insertion device 210 (and any instruments which may have been placed through the insertion device).

Figure 6H:
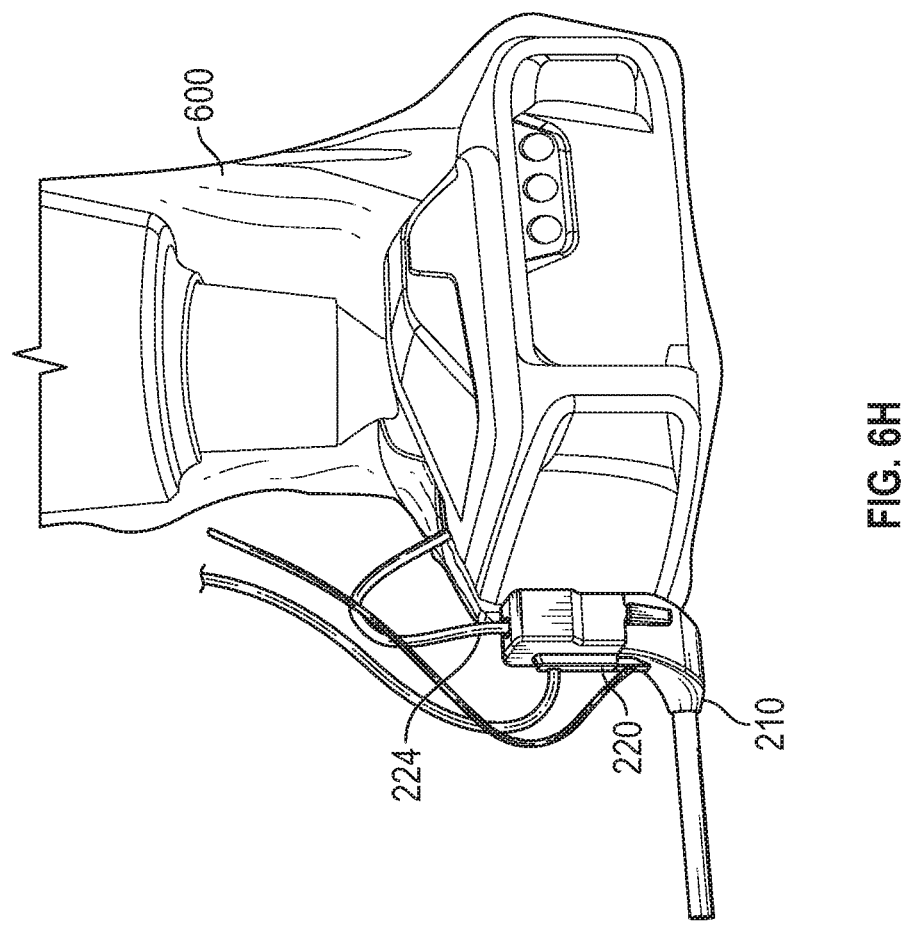
Figure 6I:
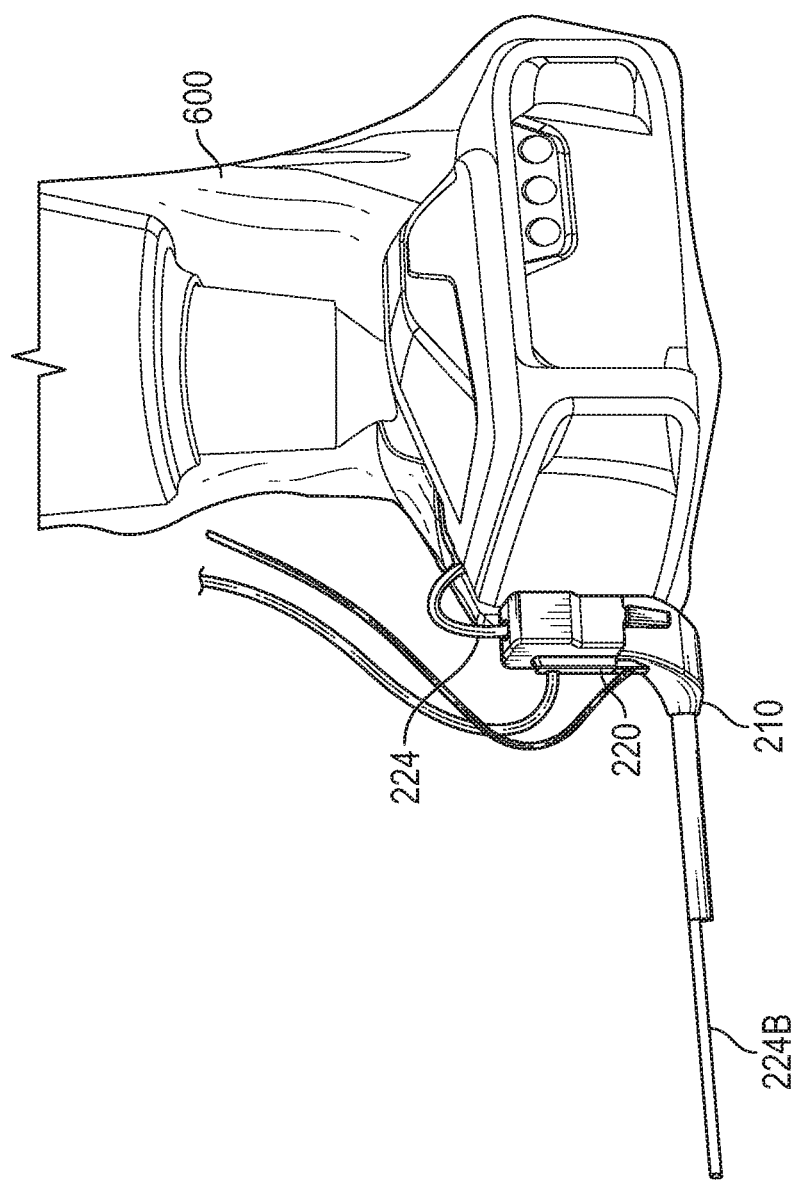

Camera tube 224 can be advanced though the visualization device 220 and inserted into the interior of the insertion device 210 as illustrated in FIG. 6H and described herein. Camera tube 224 can be further advanced through the interior of the insertion device 210 so that the distal end 224B exits the insertion device 210 as illustrated in FIG. 6I and described herein. The distal end 224B of the camera tube 224 can be advanced near or into the site of interest. Then, one or more instruments (which can be sterile) can be inserted and advanced near or into the site of interest.

In some cases, a user, such as a nurse, can insert one or more instruments, dock one or more of the visualization device or insertion device on the mounting interface 500, and advance and/or retract the camera tube 224. A surgeon operating the robotic surgical system 100 can cause the camera tube 224 to be advanced and/or retracted. For example, the surgeon can operate the camera tube 224 once the distal end 224B of the camera tube has been inserted into the opening 410 and past opening 412.

Operation of a Visualization Device

As described herein, the visualization device 220 can include an imager, such as the imager 430 illustrated in FIG. 4B. The imager can be positioned at or near the tip of the distal end 224B of the camera tube 224. As described below, the imager can be oriented in various positions in the camera tube 224.

Figure 7A:
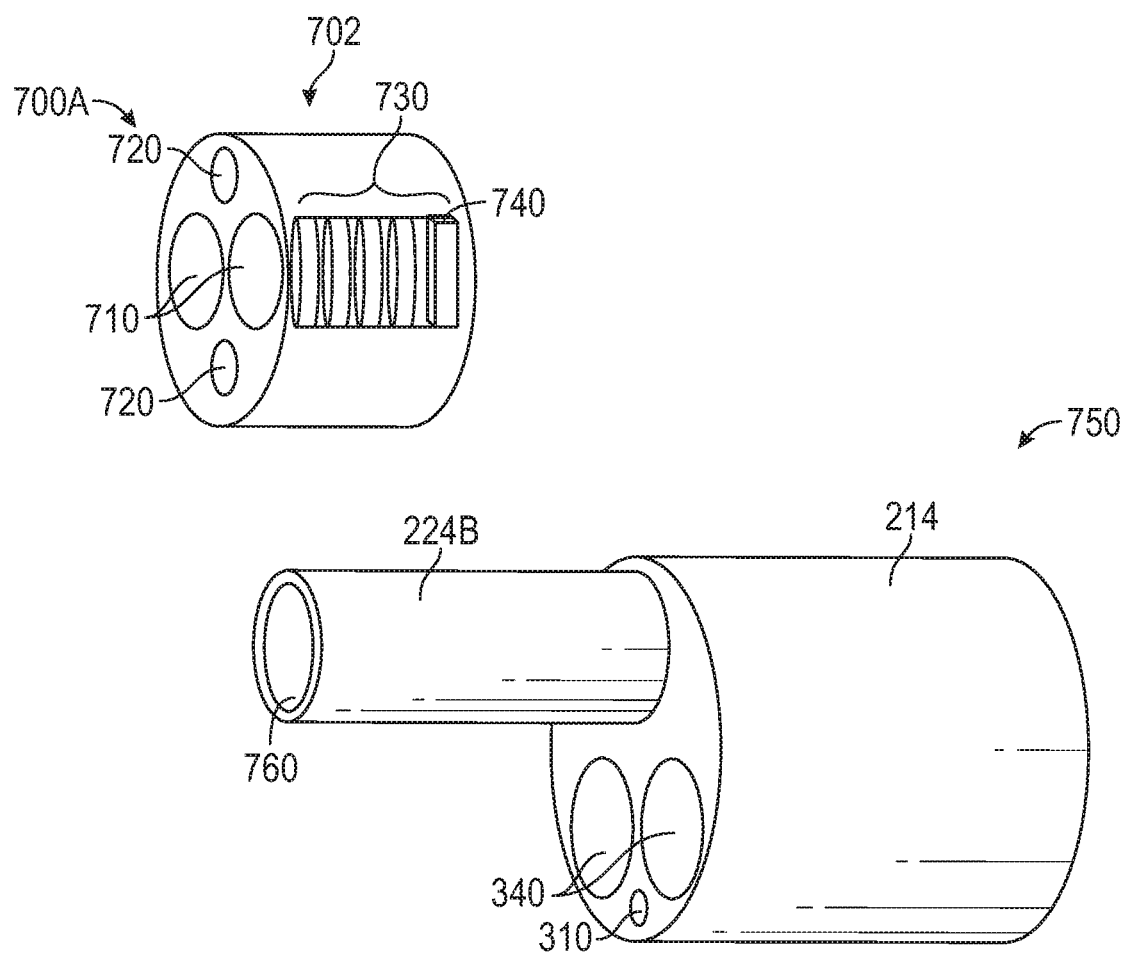
FIGS. 7A-7H and 8 illustrate visualization devices with imagers according to some embodiments.

FIG. 7A illustrates a combination 700A of an image module or imager 702, which can be similar to the imager 430, and a distal end 750 of the insertion device 210. The imager 702 can include one or more cameras 710 and one or more illumination channels 720 in which one or more illumination devices can be positioned. The one or more illumination devices can illuminate at least a portion of the site of interest to permit viewing of the at least one portion. The one or more illumination devices can include one or more light sources, such as light emitting diodes (LEDs), optical fibers, or the like. As illustrated, in some cases, two (or more) cameras 710 can be used in order for the imager 702 to operate as a stereoscopic imager, and to produce three-dimensional representation of at least a portion of the site of interest. Each of the cameras 710 can include one or more lenses 730 that focus light from and/or reflected by at least the portion of the site of interest on an image sensor 740. The one or more lenses 730 can include concave and/or convex lenses. In some cases, one or more lenses 730 can be moved to adjust the zoom (such as, an optical zoom). The image sensor 740 can detect the light and convert it to image information or data. For instance, the image sensor 740 can measure brightness at a plurality of points. The image sensor 740 can include at least one of charge-coupled devices (CCDs), complementary metal-oxide-semiconductor (CMOS) image sensors, or the like. The image sensor 740 can be a digital and/or analog image sensor. In some implementations, one camera 710 can be used or more than two cameras can be used.

The imager 702 can be positioned in the camera tube 224, such as at or near the tip of the distal end 224B of the camera tube. For example, the imager 702 can be at least partially inserted into the camera tube 224. As illustrated in FIG. 7A and described herein, the camera tube 224 with the distal end 224B can be inserted in a channel of the plurality of channels 214 of the insertion device 210. As described herein, such channel can be the channel 320. A protector 760 (such as glass or plastic) can be positioned in the camera tube 224 closer to the tip than the imager 702. The protector 760 can protect the imager 702 from breaking or malfunctions due to, for example, coming into contact with fluid in the site of interest. The imager 702 can serve as the primary camera as described herein. A secondary camera can be positioned in the channel 310 as described herein.

In some cases, the imager 702 can be included inside an imaging module (not shown) that may be hermetically sealed and that is coupled or otherwise mounted to the distal end 224B of the camera tube. The imaging module enclosing the imager 702 could be removably mounted and allow the ability to have the imaging module and camera tube 224 manufactured and/or packaged at separate locations. A variety of imaging modules (for example, with different orientations) can be provided as described herein.

Figure 7B:
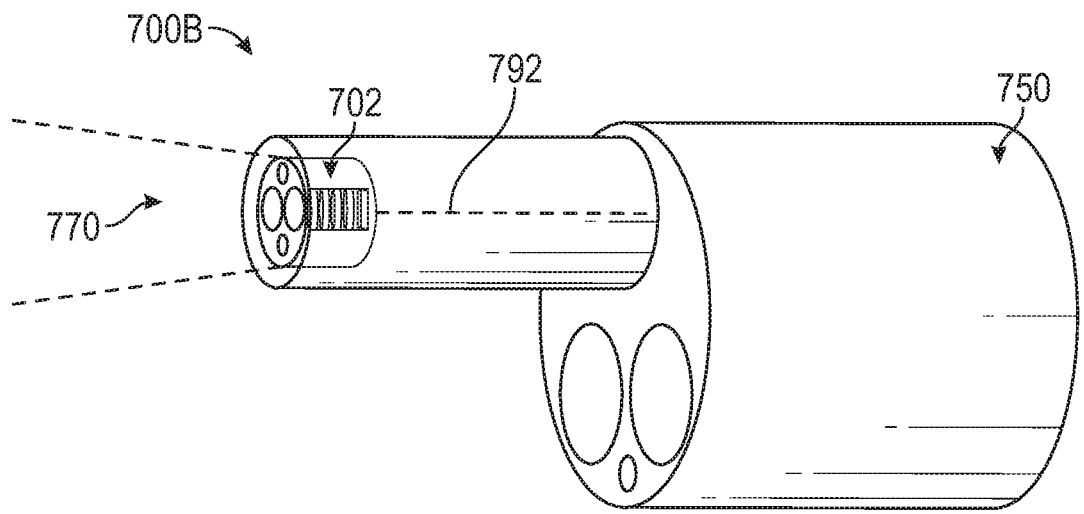

Different orientations of the imager 702 in the camera tube 224 of the visualization device 220 can provide different advantages for exploring the site of interest. In some embodiments, the imager 702 can be positioned along or substantially along a central axis 792 of the distal end 224B of the camera tube 224 as illustrated in an arrangement 700B of FIG. 7B. In such orientation, the imager is not tilted down or up with respect to the distal end 224B of the camera tube when the proximal end is extended away from the insertion device 210 toward the site of interest. A field of view 770 of the imager 702, which can represent an area or region in which the imager obtains or captures image data, can be oriented along or substantially along the central axis 792. The field of view 770 can encompass a region straight ahead of the distal end 224B of the camera tube 224.

Advantageously, in some cases, the imager 702 of the arrangement 700B can provide image data of at least a portion of the site of interest when the site is positioned in front of the insertion device 210. For example, the imager 702 can "look straight ahead" or provide image data of a region in front as the distal end 224B of the camera tube 224 exits the channel of the insertion device 210. When the insertion device 210 is positioned adjacent the site of interest, imager positioning in the arrangement 700B can permit viewing the site of interest. This can be important, for example, to facilitate safe insertion of at least a portion of the distal end 224B (along with, for example, the primary camera) into the site of interest.

Figure 7C:
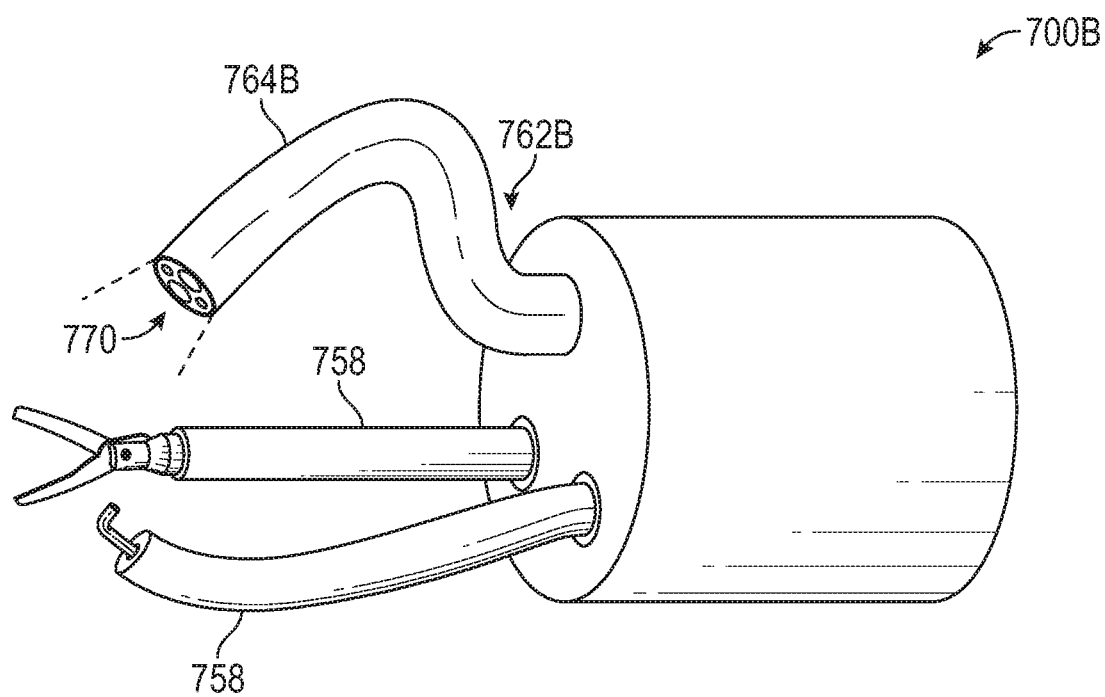

In some cases, the one or more channels 340 are positioned below the channel 320 through which the distal end 224B of the camera tube 224 is passed. With reference to FIG. 7C, when one or more instruments are inserted through one or more channels 340, it may be desirable to orient the imager 702 of the arrangement 700B to obtain a field of view oriented at least partially downward. For example, the imager 702 can be positioned to "look down" at the one or more instruments. Orienting the field of view 770 at least partially downward can advantageously permit viewing of the insertion of one or more instruments 758 into the site of interest. This can facilitate safe insertion of the one or more instruments into the site of interest.

As illustrated in FIG. 7C, in order to orient the field of view 770 at least partially downward, the distal end 224B of the camera tube 224 may be bent along a plurality of segments or sections 762B and 764B. As described herein, section 764B can correspond to the tilt section 442, and section 762B can correspond to the pan section 444. Both sections 762B and 764B may be bent to orient the imager 702 to provide image data relating to the position of the one or more instruments 758.

Figure 7D:
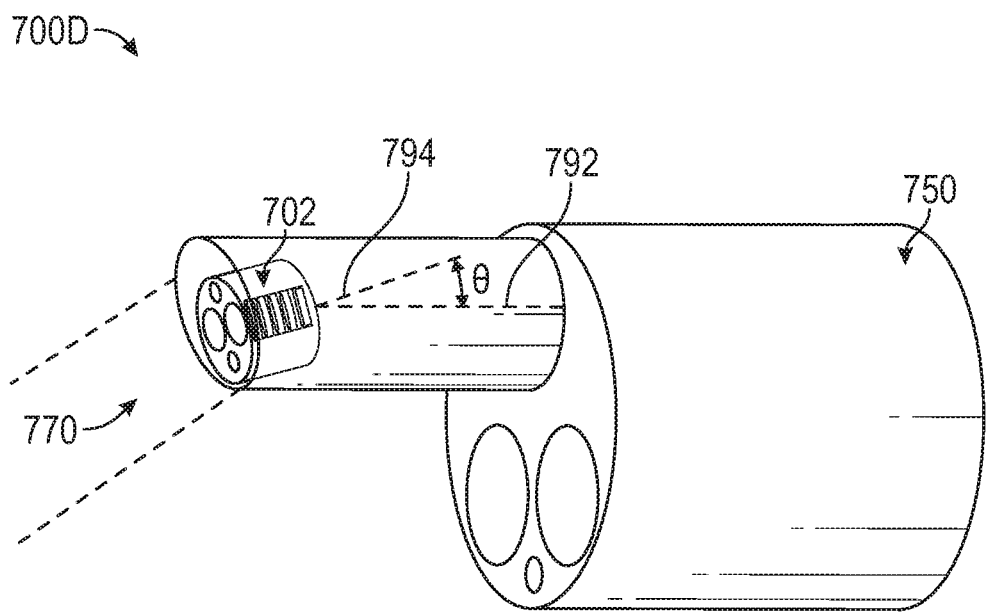

FIG. 7D illustrates an arrangement 700D in which the imager 702 is tilted downward at an angle θ relative to the central axis 792. The angle θ is formed between the central axis 792 and a central axis 794 of the imager 702. The angle θ can be 10 degrees or less or more, 15 degrees or less or more, 20 degrees or less or more, or the like. Tilting the imager 702 downward can cause the field of view 770 to be oriented at least partially downward. Advantageously, the field of view 770 can capture at least a portion of the region in front (which, for example, can be the site of interest as described herein) as well as at least a portion of the region below the imager 702. The arrangement 700D can permit viewing of the position of the one or more instruments 758 as well as viewing of at least the portion of the site of interest. This can facilitate insertion of both the primary camera and the one or more instruments 758.

Figure 7E:
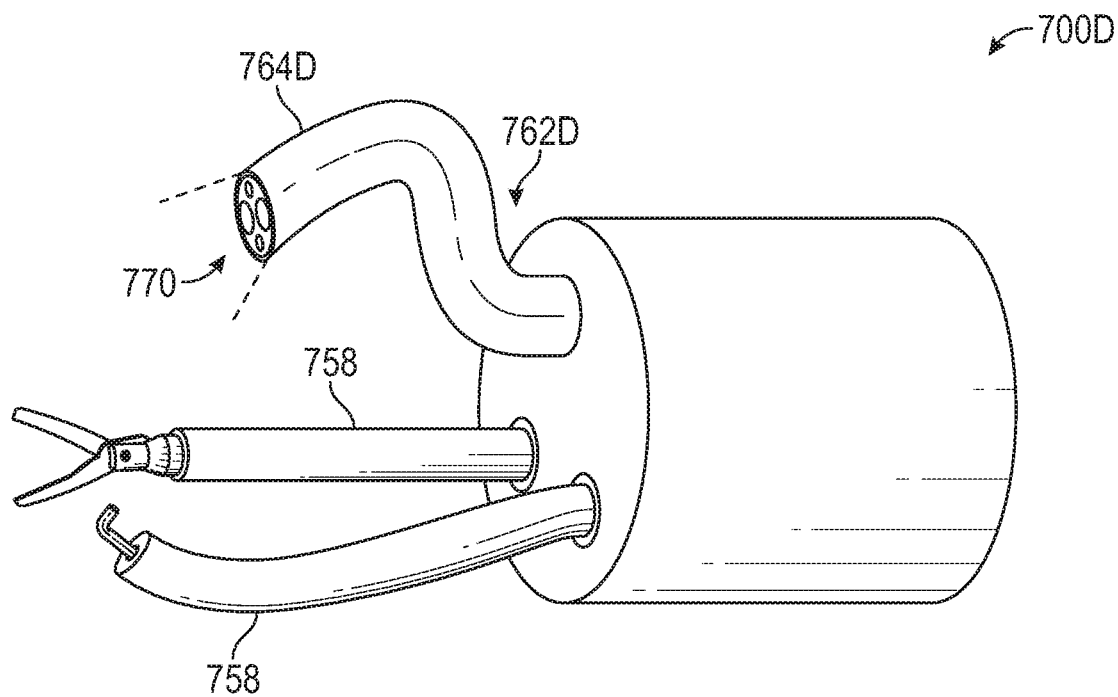

As illustrated in FIG. 7E, the field of view 770 in the arrangement 700D can be further oriented downward by bending the distal end 224B of the camera tube 224 along a plurality of segments or sections 762D and 764D. These sections can be similar to sections 762B and 764B of the arrangement 700B (shown in FIG. 7C), respectively. The angle or curvature of the bend in at least one of the sections 762D and 764D can be smaller than in at least one of the sections 762B and 764B, respectively. This reduction can be due to initially tilting the imager 702 downward at the angle θ.

Figure 7F:
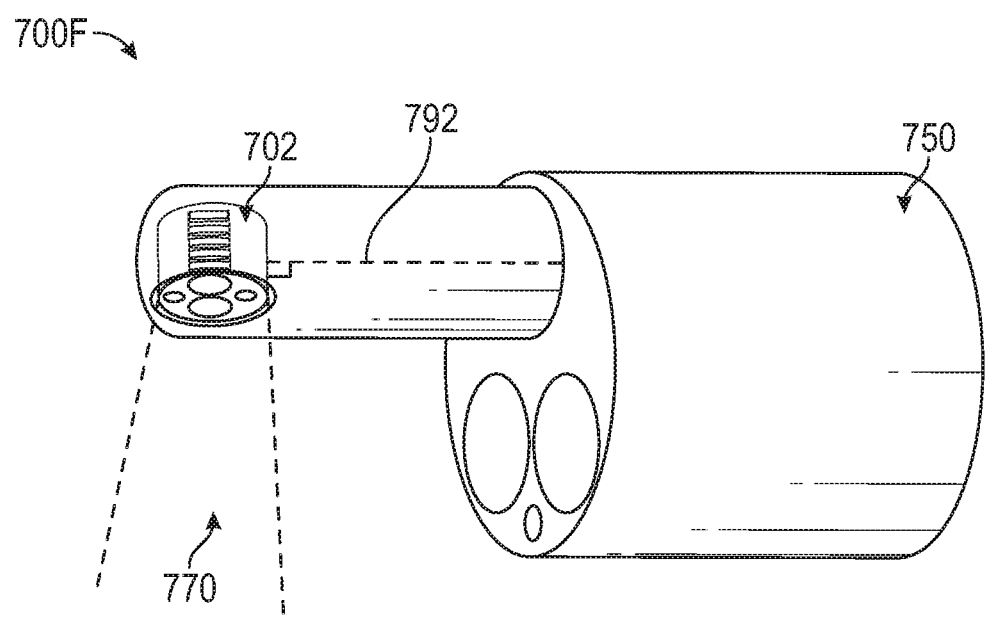
Figure 7G:
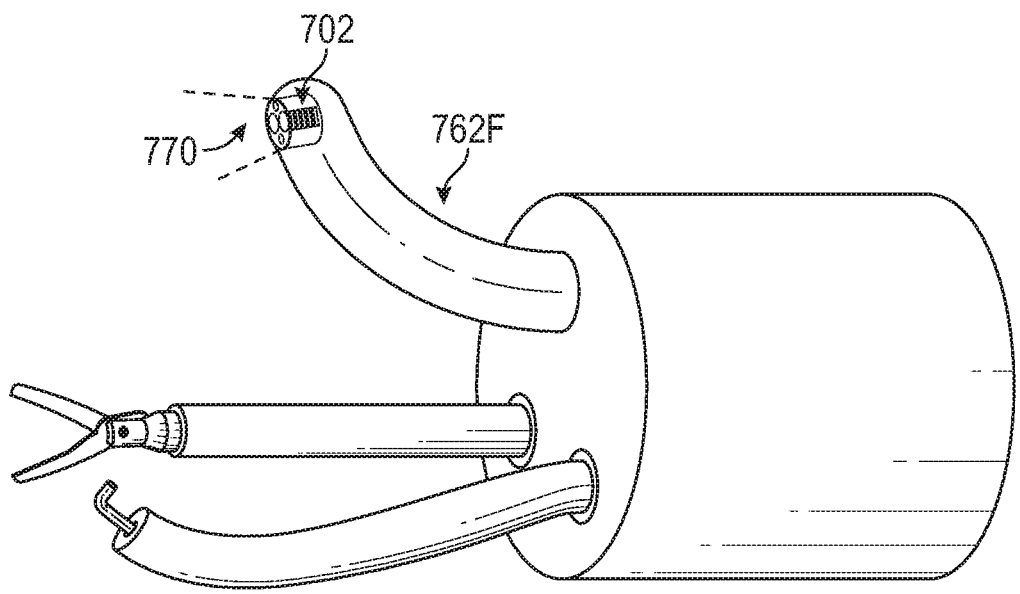

FIG. 7F illustrates an arrangement 700F in which the imager 702 is positioned downward at approximately 90 degree angle relative to the central axis 792. The field of view 770 captures a region below the imager 702. This can be advantageous to facilitate insertion of the one or more instruments 758. The field of view 770 may not capture or substantially not capture at least a portion of the region in front of the imager 702. In order to capture at least the portion of this region, the distal end 224B of the camera tube 224 can be bent along a segment or section 762F as illustrated in FIG. 7G. This orientation can facilitate insertion of the primary camera. Comparing with the arrangements 700B and 700D, adjustment of the orientation of a single segment 762F may be sufficient.

Figure 7H:
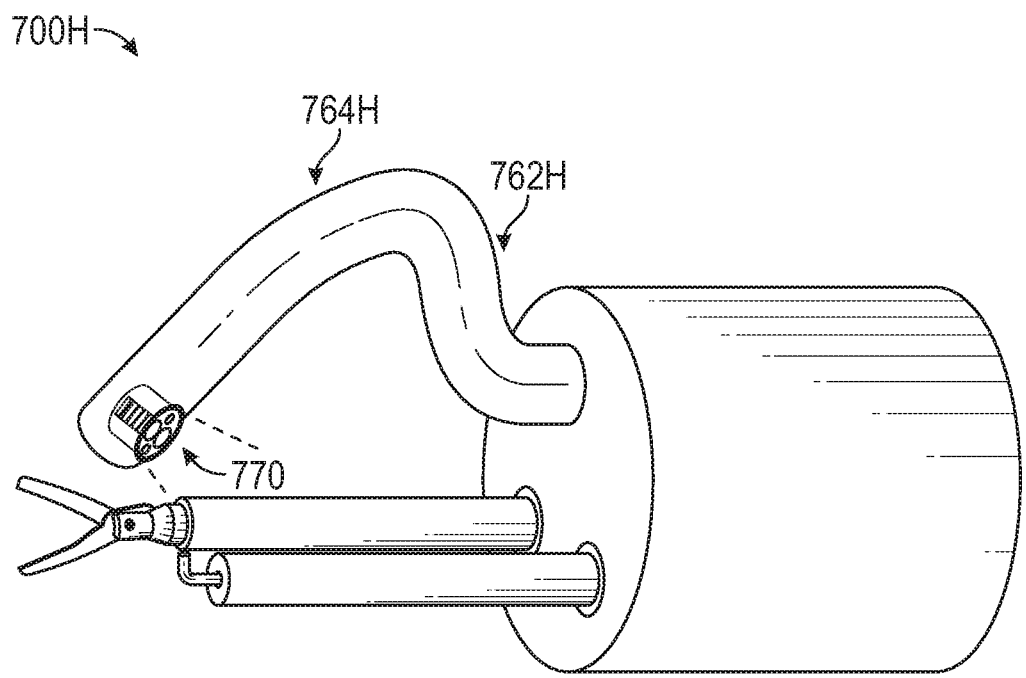

As illustrated in arrangement 700H of FIG. 7H, in order to capture at least a portion of a region behind the imager 702, the distal end 224B of the camera tube 224 may be bent along a plurality of segments or sections 762H and 764H. These sections can similar to sections 762B and 764B of the arrangement 700B, respectively. The field of view 770 of the arrangement 700H can permit viewing of the one or more instruments 758 being advanced through the one or more channels in the insertion device 210.

Figure 8:
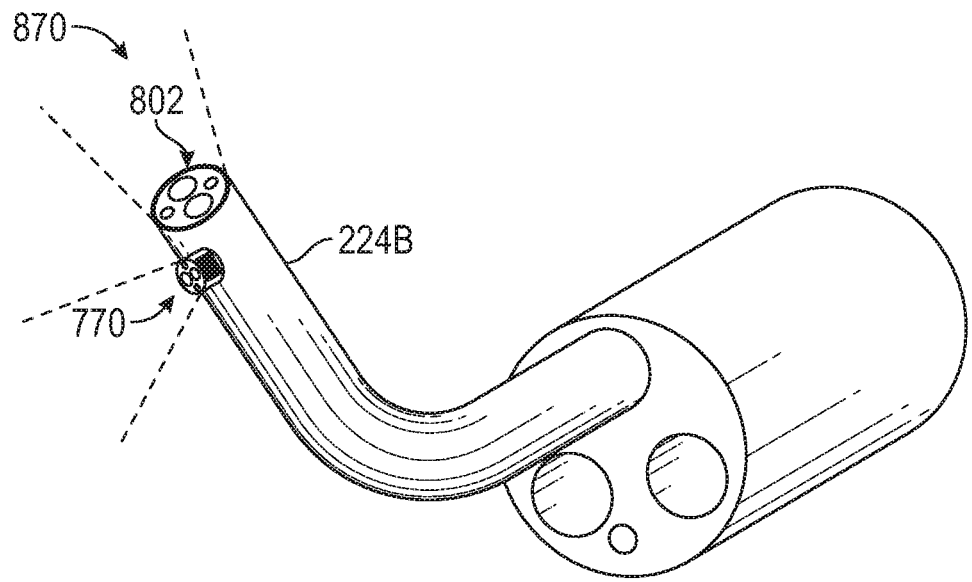

In some cases, a second or another imager can be provided in the arrangement 700F, in which the imager 702 is positioned substantially downward. For example as illustrated in FIG. 8, such second imager 802 can be positioned along or substantially along the central axis of the distal end 224B of the camera tube 224 similarly to the arrangement 700B. The second imager 802 can provide an additional field of view 870 to the field of view 770 of the imager 702. The field of view 870 can capture at least a portion of the region in front of the second imager 802. This can facilitate insertion of the primary camera, which can include both imagers 702 and 802.

In some implementations, the imager 702 can be tilted up. For example, this can be advantageous when one or more channels through which one or more instruments are inserted are positioned above the channel 320 through which the distal end 224B of the camera tube 224 is passed.

As described herein, the imager 702 can be oriented differently relative to the central axis 792 of the distal end 224B of the camera tube 224. The imager 702 can be positioned substantially along the central axis 792, perpendicular to the central axis, or at any angle between 0 degrees and 90 degrees (facing up or down) relative to the central axis. Varying the orientation of the imager 702 can adjust the orientation of the field of view 770 of the imager. A suitable orientation of the imager 702 can be selected based on a desired field of view 770.

In some cases, one or more actuators configured to adjust orientation of the imager 702 can be provided. For example, the one or more actuators can include one or more motors. Advantageously, orientation of the imager 702 can be adjusted in operation.

Movement of Primary Camera

Figures 9A, 9B:
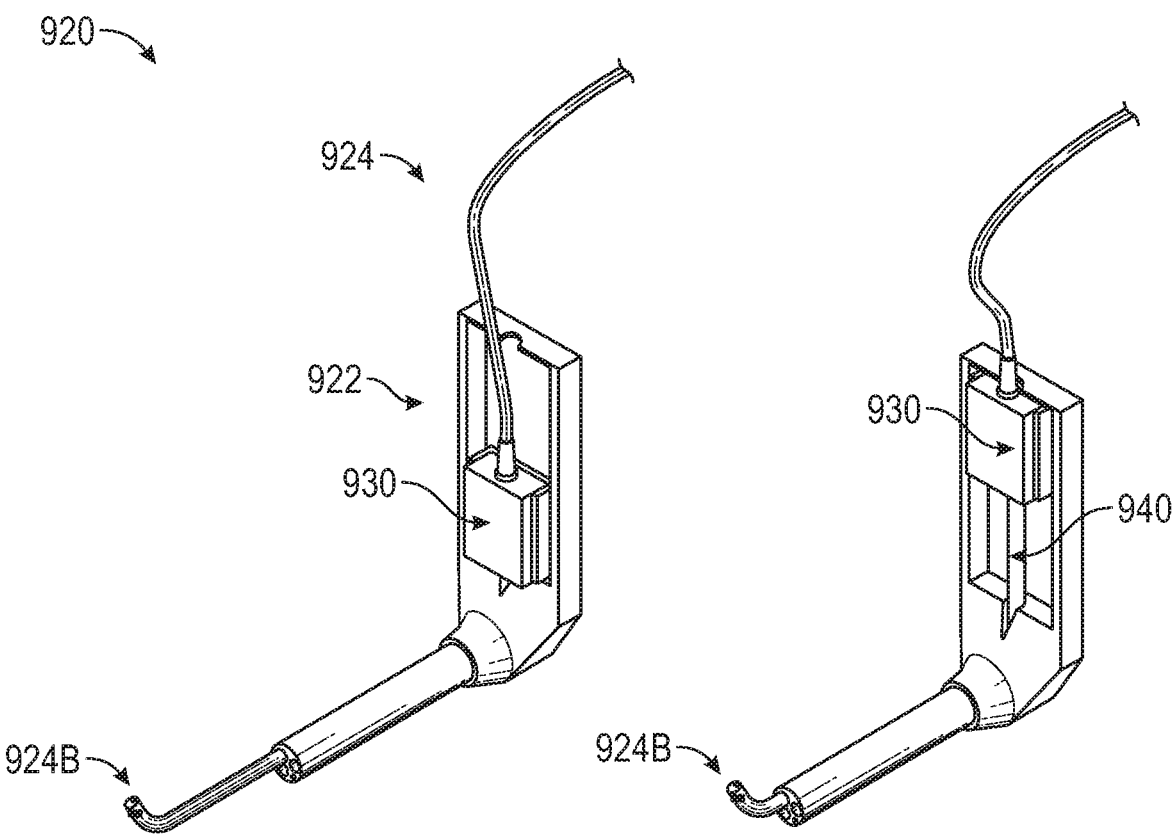
FIGS. 9A-9B and 10A-10B illustrate visualization and/or insertion devices according to some embodiments.

Other mechanisms for advancing and/or retracting a camera tube can be used. In some cases, a movement device can travel along with the camera tube. For example, FIGS. 9A-9B illustrate an insertion and/or visualization device 920 with a movement device 930 configured to travel vertically (or, in some cases, horizontally) to advance and/or retract a camera tube 924. FIG. 9A illustrates a distal end 924B of the camera tube 924 extending at a maximum distance toward the site of interest (such as, fully extended). In this position, the movement device 930 is moved downward, such as to the bottom position in a housing 922, to advance the distal end 924B. FIG. 9B illustrates the distal end 924B of the camera tube 924 extending at a maximum distance away from the site of interest (such as, fully retracted). In this position, the movement device 930 is moved upward, such as to the top position in the housing 922, to retract the distal end 924B.

The movement device 930 can include one or more actuators (for example, one or more motors) that move the movement device up and/or down (or, in some cases, left and/or right) within the housing 922. For example, the movement device 930 can move along a rail or post 940. In some cases, the rail 940 can include a chain for facilitating or guiding movement of the movement device. The movement device can include additional one or more actuators configured to tilt and/or pan one or more cameras positioned in the camera tube 924.

Figure 10A:
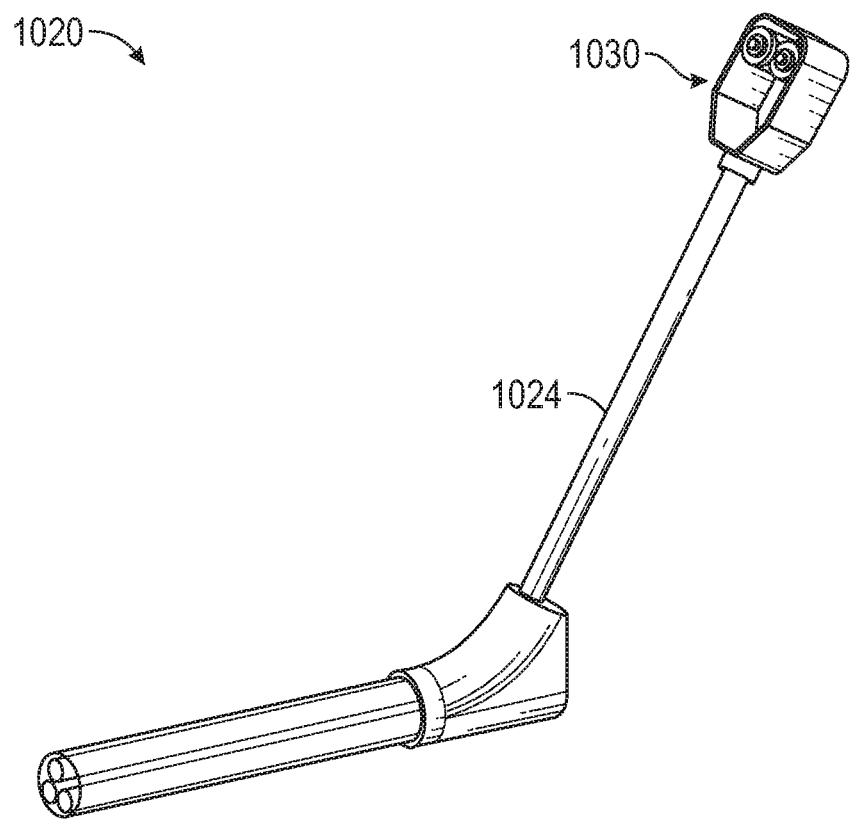
Figure 10B:
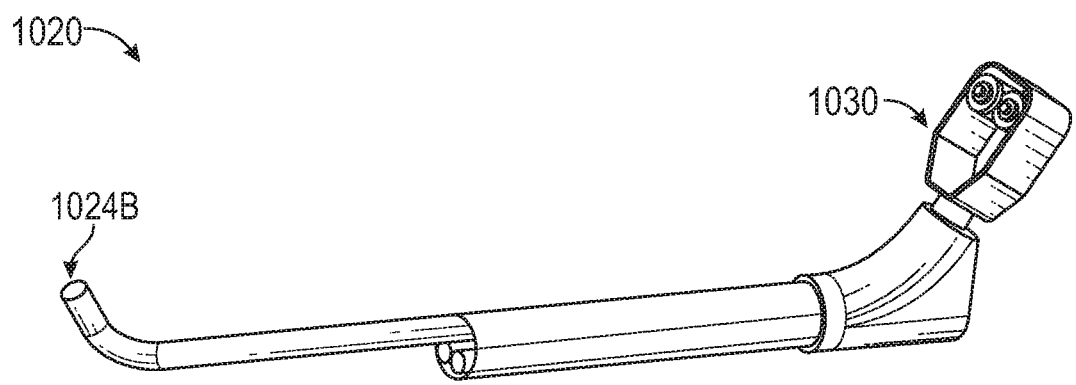

As illustrated in FIGS. 10A-10B, a movement device 1030 may be positioned outside and/or away from a housing of an insertion and/or visualization device 1020. The movement device 1030 can move downward to advance a distal end 1024B of a camera tube toward the site of interest. The movement device 1030 can move upward to retract the distal end 1024B. As illustrated, the movement device 1030 can downward and/or upward at an angle to the vertical axis.

Figure 11:
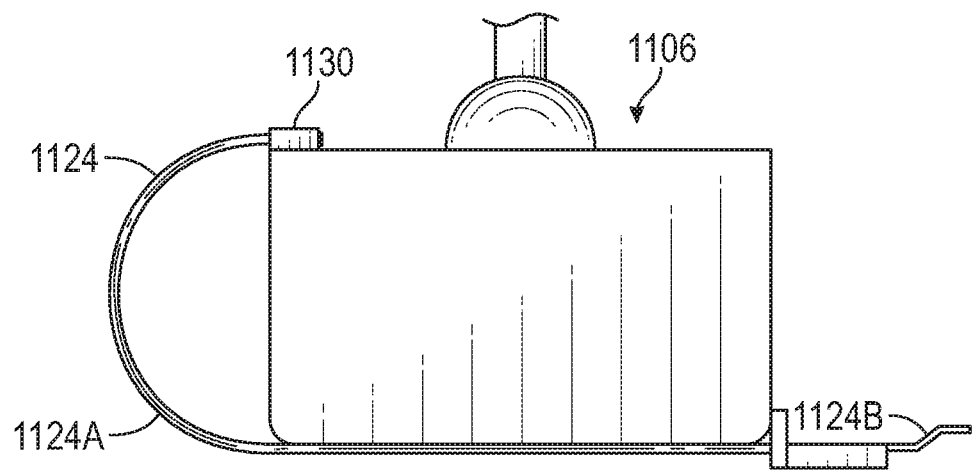
FIGS. 11 and 12A-12D illustrate drive units of a robotic surgery system according to some embodiments.

In some cases, a movement device can be substantially stationary and the camera tube may not form a loop as described herein. For example, FIG. 11 illustrates a drive unit 1106 supporting (for example, on top) a movement device 1130 configured to advance and/or retract a camera tube 1124 that includes a proximal end 1124A and a distal end 1124B. The movement device 1130 can advance and/or retract the distal end 1124B of the camera tube 1124 along substantially horizontal direction (or, in some cases, a vertical direction). The proximal end 1124A of the camera tube 1124 can provide "slack" or sufficient camera tube length to advance the distal end 1124B to a maximum distance toward the site of interest (or away from the drive unit 1106). In some cases, the movement device 1130 can be positioned at another location on the drive unit 1106 or be supported by another component of a robotic surgery system.

Figure 12A:
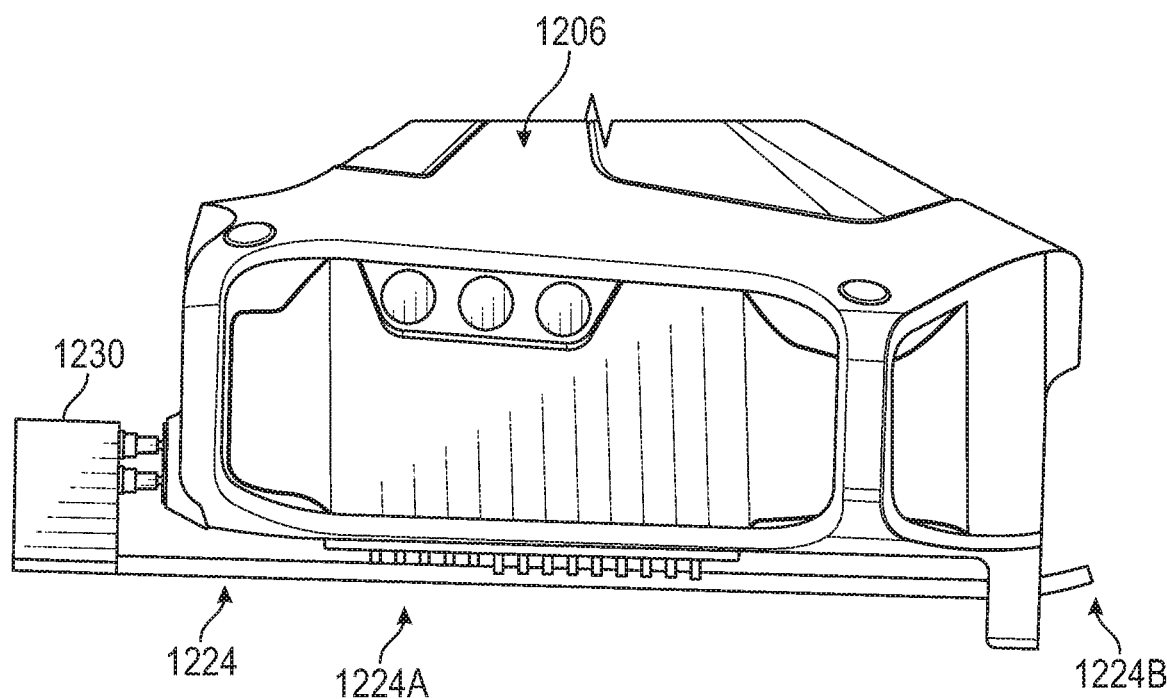
Figure 12B:
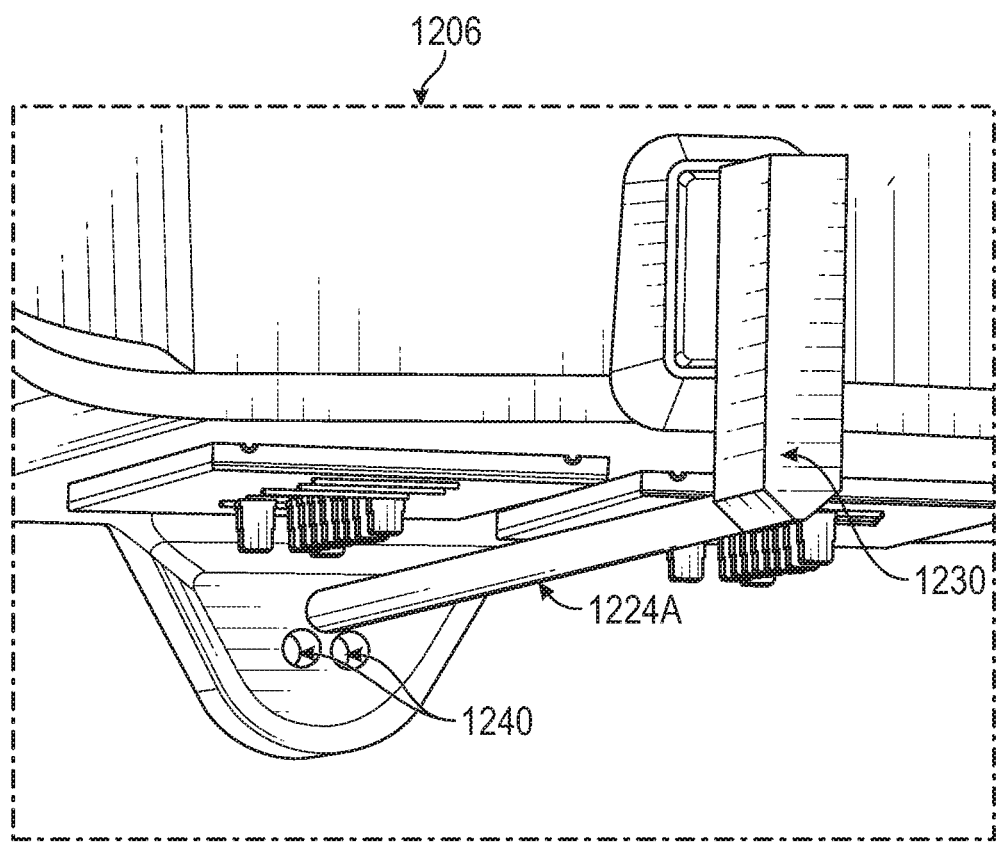

In some cases, at least a portion of the camera tube can be substantially rigid. For example, FIG. 12A illustrates perspective view of a movement device 1230 supported by a drive unit 1206. The movement device 1230 can be positioned at the rear of the drive unit 1206. The movement device 1230 can be configured to advance and/or retract a camera tube 1224 that includes a proximal end 1224A and a distal end 1224B. FIG. 12B illustrates a bottom view showing one or more openings 1240 for one or more instruments (not shown). In operation, the one or more instruments can be positioned adjacent to the camera tube 1224. In some cases, the movement device 1230 can be positioned at another location on the drive unit 1206 or be supported by another component of a robotic surgery system.

Figure 12C:
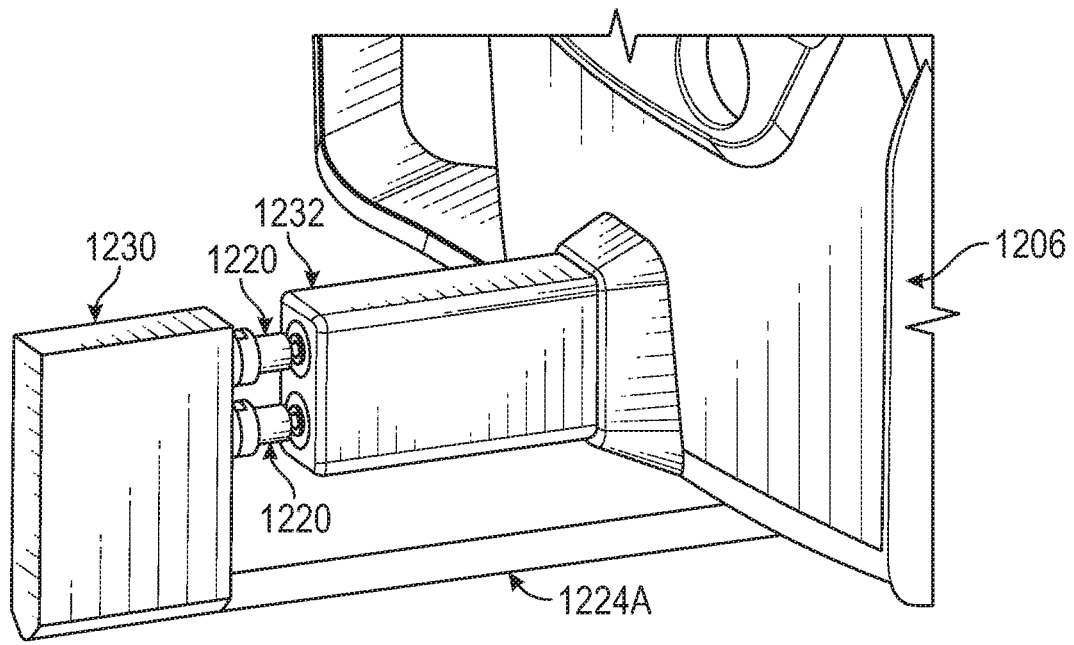

FIG. 12C illustrates the camera tube extending at maximum distance away from the site of interest (such as, fully retracted). In this position, a movement portion or mover 1232 can be fully retracted. For example, the mover 1232 can retracted backward and oriented outside an interior portion of the drive unit 1206. Movement of the mover 1232 can cause the movement device 1230 to move in the same direction. The camera tube 1224 can be attached or connected to the movement device 1230, and movement of the movement device 1230 can cause the camera tube 1224 to move in the same direction. Also illustrated are one or more actuators 1220 configured to control tilt and/or pan of one or more cameras positioned in the camera tube 1224.

Figure 12D:
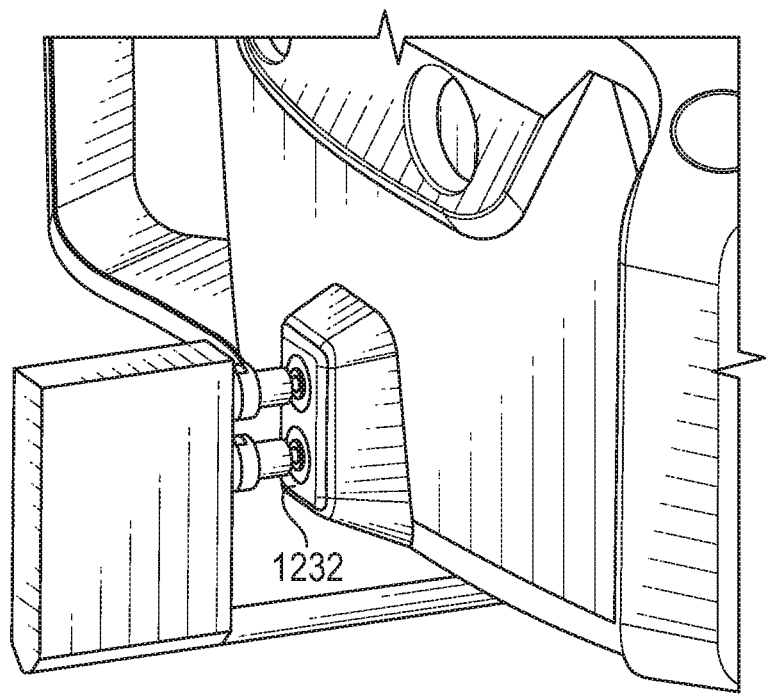

FIG. 12D illustrates the camera tube extending at maximum distance toward the site of interest (such as, fully extended). In this position, the mover 1232 can be fully extended. For example, the mover 1232 can be extended forward and oriented in the interior portion of the drive unit 1206. As described, at least a portion of the camera tube 1224 can be substantially rigid at least because the proximal end 1224A may be maintained as substantially straight. For instance, the proximal end 1224A may not be bent in contrast with, for example, in FIG. 11). The proximal end 1224A can include the substantially rigid portion. Advantageously, having the substantially rigid portion may prevent the camera tube 1224 coming into contact with unsterile surface or object, such as the floor, because of the length of the slack.

Advantageously, using a visualization device configured to cause the camera tube to form a loop as described herein can reduce or eliminate the risk of a camera tube coming into contact with an unsterile surface or object. Advantageously, drivers configured to rotate (such as, rollers) to advance/retract the camera tube as described herein can facilitate reducing the size of a visualization device.

OTHER VARIATIONS

Those skilled in the art will appreciate that, in some embodiments, additional components and/or steps can be utilized, and disclosed components and/or steps can be combined or omitted. For example, although some embodiments are described in connection with a robotic surgery system, the disclosure is not so limited. Systems, devices, and methods described herein can be applicable to medical procedures in general, among other uses. As another example, certain components can be illustrated and/or described as being circular or cylindrical. In some implementations, the components can be additionally or alternatively include non-circular portions, such as portions having straight lines. As yet another example, any of the actuators described herein can include one or more motors, such as electrical motors. As yet another example, in addition to or instead of controlling tilt and/or pan of a camera, roll (or spin) can be controlled. For example, one or more actuators can be provided for controlling the spin.

The foregoing description details certain embodiments of the systems, devices, and methods disclosed herein. It will be appreciated, however, that no matter how detailed the foregoing appears in text, the systems, devices, and methods can be practiced in many ways. The use of particular terminology when describing certain features or aspects of the disclosure should not be taken to imply that the terminology is being redefined herein to be restricted to including any specific characteristics of the features or aspects of the technology with which that terminology is associated.

It will be appreciated by those skilled in the art that various modifications and changes can be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures can be combined, interchanged, or excluded from other embodiments.

With respect to the use of substantially any plural and/or singular terms herein, those having skill in the art can translate from the plural to the singular and/or from the singular to the plural as is appropriate to the context and/or application. The various singular/plural permutations can be expressly set forth herein for sake of clarity.

Directional terms used herein (for example, top, bottom, side, up, down, inward, outward, etc.) are generally used with reference to the orientation or perspective shown in the figures and are not intended to be limiting. For example, positioning "above" described herein can refer to positioning below or on one of sides. Thus, features described as being "above" may be included below, on one of sides, or the like.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations).

The term "comprising" as used herein is synonymous with "including," "containing," or "characterized by," and is inclusive or open-ended and does not exclude additional, unrecited elements or method steps.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function and/or achieves a desired result. For example, the terms "approximately", "about", "generally," and "substantially" may refer to an amount that is within less than 10% of, within less than 5% of, within less than 1% of, within less than 0.1% of, and/or within less than 0.01% of the stated amount.

It will be further understood by those within the art that any disjunctive word and/or phrase presenting two or more alternative terms, whether in the description, claims, or drawings, can be understood to contemplate the possibilities of including one of the terms, either of the terms, or both terms. For example, the phrase "A or B" will be understood to include the possibilities of "A" or "B" or "A and B." Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The above description discloses embodiments of systems, apparatuses, devices, methods, and materials of the present disclosure. This disclosure is susceptible to modifications in the components, parts, elements, steps, and materials, as well as alterations in the fabrication methods and equipment. Such modifications will become apparent to those skilled in the art from a consideration of this disclosure or practice of the disclosure. Consequently, it is not intended that the disclosure be limited to the specific embodiments disclosed herein, but that it cover all modifications and alternatives coming within the scope and spirit of the subject matter embodied in the following claims.

What is claimed is:

1. A visualization device for a single port robotic surgery apparatus, the visualization device comprising:
a housing configured to be removably attached to a mounting interface of the robotic surgery apparatus and be positioned adjacent an insertion device of the robotic surgery apparatus, the housing comprising first and second openings positioned on an exterior of the housing, wherein the housing includes a pair of drivers disposed on opposite sides of the first opening; and
a flexible camera tube including a first end attached to and extending proximally from a first position on the housing and a second end comprising at least one camera, the second end configured to be flexed in first direction to form a loop around at least a portion of the housing and inserted through the first opening in the housing, pass through an interior of the housing where the second end is flexed in a second direction, opposite the first direction, and exit the housing through the second opening in the housing, the second end configured to extend away from the second opening on the housing toward a region of interest outside the housing or retract away from the region of interest and back toward the housing, wherein the position of the second opening on the housing is separate and apart from the first position on the housing such that a central longitudinal axis of the first end of the camera tube is not axially aligned with a central longitudinal axis of the second end of the camera tube when the second end of the camera tube extends away from the position of the second opening on the housing,
wherein, the pair of drivers are configured to move the flexible camera tube through the first and second openings in the housing so that a distal end of the flexible camera tube extends away from the second opening of housing or retracts back into the second opening of the housing.

2. The device of claim 1, wherein the first opening and the second opening are parallel and spaced apart such that they are positioned on opposite sides of the housing.

3. The device of claim 1, wherein an orientation of the first opening is aligned with an orientation of the second opening such that the camera tube positioned in the interior of the housing is configured to be linear when passing between the first opening and the second opening.

4. The device of claim 1, wherein the region of interest comprises a body cavity into which an end effector is configured to be inserted.

5. The device of claim 1, wherein the first end of the camera tube is removably attached to the housing.

6. The device of claim 1, wherein the housing is configured to receive at least one driver configured to cause movement of the camera tube away from the housing and/or toward the housing.

7. The device of claim 6, wherein the camera tube is configured to form a loop around at least a portion of the housing.

8. The device of claim 6, wherein the at least one driver comprises a plurality of rollers, and wherein the camera tube is configured to contact the plurality of rollers and advance toward the region of interest and retract away from the region of interest in response to rotation of the plurality of rollers.

9. The device of claim 8, wherein the camera tube is configured to advance and decrease a diameter of the loop in response to rotation of the plurality of rollers in a first direction, and wherein the camera tube is configured to retract and increase the diameter of the loop in response to rotation of the plurality of rollers in a second direction opposite the first direction.

10. The device of claim 1, wherein the first opening is positioned on a first exterior surface of the housing, wherein the second opening is positioned on a second exterior surface of the housing, and wherein the first and second exterior surfaces are parallel to each other.

11. The device of claim 10, wherein the first end of the camera tube is attached to a third exterior surface of the housing, and wherein the third exterior surface is perpendicular to the first exterior surface.

12. A kit comprising the visualization device of claim 1 and an insertion device.

13. The kit of claim 12, wherein the insertion device comprises a passage positioned in an interior volume of the insertion device, the passage configured to permit the second end of the camera tube to pass through and exit the insertion device, and wherein the insertion device comprises at least one instrument channel configured to receive a surgical instrument.

14. The kit of claim 13, wherein a central axis of at least a portion of the passage is nonparallel with a central axis of the at least one instrument channel.

15. The kit of claim 13, wherein the at least one instrument channel is substantially straight and at least a portion of the passage is curved.

16. The kit of claim 12, wherein the housing, camera tube, and the insertion device are sterile.

17. The device of claim 1, wherein the flexible camera tube is positioned between the pair of drivers, whereby rotation of the pair of drivers in a first direction extends the distal end of the flexible camera away from the second opening of housing, and whereby rotation of the pair of drivers in a second direction, opposite to the first direction, retracts the distal end of the flexible camera back into the second opening of the housing.

18. The device of claim 17, wherein an external surface of the pair of rollers is fabricated from a friction enhancing material for gripping an outer surface of the flexible camera tube.

19. The device of claim 17, wherein an external surface of the pair of rollers includes a friction enhancing features for gripping an outer surface of the flexible camera tube.

20. A visualization device for a single port robotic surgery apparatus, the visualization device comprising:
a housing configured to be removably attached to a mounting interface of the robotic surgery apparatus and be positioned adjacent an insertion device of the robotic surgery apparatus, the housing comprising first and second openings positioned on an exterior of the housing, wherein the housing includes a pair of drivers disposed on opposite sides of the first opening; and
a flexible camera tube including a first end attached to and extending proximally from a first position on the housing and a second end comprising at least one camera, the second end configured to be flexed in a direction to form a loop and inserted through the first opening in the housing, pass through an interior of the housing, and exit the housing through the second opening in the housing, the second end configured to extend away from the second opening on the housing toward a region of interest outside the housing or retract away from the region of interest and back toward the housing, wherein the position of the second opening on the housing is separate and apart from the first position on the housing such that a central longitudinal axis of the first end of the camera tube is not axially aligned with a central longitudinal axis of the second end of the camera tube when the second end of the camera tube extends away from the position of the second opening on the housing,
wherein, the pair of drivers are configured to move the flexible camera tube through the first and second openings in the housing so that a distal end of the flexible camera tube extends away from the second opening of housing or retracts back into the second opening of the housing.

21. The device of claim 20, wherein the flexible camera tube is positioned between the pair of drivers, whereby rotation of the pair of drivers in a first direction extends the distal end of the flexible camera away from the second opening of housing, and whereby rotation of the pair of drivers in a second direction, opposite to the first direction, retracts the distal end of the flexible camera back into the second opening of the housing.

22. The device of claim 21, wherein an external surface of the pair of rollers is fabricated from a friction enhancing material for gripping an outer surface of the flexible camera tube.

23. The device of claim 21, wherein an external surface of the pair of rollers includes a friction enhancing features for gripping an outer surface of the flexible camera tube.

24. A visualization device for a single port robotic surgery apparatus, the visualization device comprising:
a housing configured to be removably attached to a mounting interface of the robotic surgery apparatus and be positioned adjacent an insertion device of the robotic surgery apparatus, the housing comprising first and second openings positioned on an exterior of the housing, wherein the housing includes a pair of drivers disposed on opposite sides of the first opening; and a flexible camera tube including a first end attached to and extending proximally from a first position on the housing and a second end comprising at least one camera, the second end configured to be inserted through the first opening in the housing, pass through an interior of the housing, and exit the housing through the second opening in the housing, the second end configured to extend away from the second opening on the housing toward a region of interest outside the housing or retract away from the region of interest and back toward the housing, wherein the position of the second opening on the housing is separate and apart from the first position on the housing such that a central longitudinal axis of the first end of the camera tube is not axially aligned with a central longitudinal axis of the second end of the camera tube when the second end of the camera tube extends away from the position of the second opening on the housing, wherein, the pair of drivers are configured to move the flexible camera tube through the first and second openings in the housing so that a distal end of the flexible camera tube extends away from the second opening of housing or retracts back into the second opening of the housing.

25. The device of claim 24, wherein the flexible camera tube is positioned between the pair of drivers, whereby rotation of the pair of drivers in a first direction extends the distal end of the flexible camera away from the second opening of housing, and whereby rotation of the pair of drivers in a second direction, opposite to the first direction, retracts the distal end of the flexible camera back into the second opening of the housing.

26. The device of claim 25, wherein an external surface of the pair of rollers is fabricated from a friction enhancing material for gripping an outer surface of the flexible camera tube.

27. The device of claim 25, wherein an external surface of the pair of rollers includes a friction enhancing features for gripping an outer surface of the flexible camera tube.

* * * * *